(12) United States Patent
McGonigle et al.

(10) Patent No.: US 6,171,839 B1
(45) Date of Patent: Jan. 9, 2001

(54) SOYBEAN GLUTATHIONE-S-TRANSFERASE ENZYMES

(75) Inventors: Brian McGonigle, Wilmington, DE (US); Daniel P. O'Keefe, Ridley Park, PA (US)

(73) Assignee: E. I. du Pont de Nemours & Company, Wilmington, DE (US)

( * ) Notice: Under 35 U.S.C. 154(b), the term of this patent shall be extended for 0 days.

(21) Appl. No.: 09/296,715

(22) Filed: Apr. 22, 1999

Related U.S. Application Data

(62) Division of application No. 08/924,747, filed on Sep. 5, 1997, now Pat. No. 6,063,570.

(51) Int. Cl.[7] ....................................................... C12N 9/10
(52) U.S. Cl. ............................................................. 435/193
(58) Field of Search ............................................. 435/193

(56) References Cited

U.S. PATENT DOCUMENTS

| | | | |
|---|---|---|---|
| 5,073,677 | 12/1991 | Helmer et al. | 800/205 |
| 5,589,614 | 12/1996 | Bridges et al. | 800/205 |

FOREIGN PATENT DOCUMENTS

| | | | |
|---|---|---|---|
| 0 256 223 | 5/1987 | (EP). | |
| 0 330 479 | 8/1989 | (EP). | |
| WO 93 01294 | 1/1993 | (WO). | |
| WO 96/23072 | 8/1996 | (WO). | |
| WO 97/11189 | 3/1997 | (WO). | |
| WO99/14337 | 9/1999 | (WO) | C12N/15/54 |

OTHER PUBLICATIONS

David C. Holt et al., Characterization of the Safener–Induced Glutathione S–Transferase Isoform II from Maize, *Planta*, 196, 295–302, 1995.

F. Droog, Plant Glutathione S–Transferases, a Tale of Theta and Tau, *J. Plant Growth Regul*, 16, 95–107, 1997.

Laura Rossini et al., Characterization of Glutathione S–Transferase Isoforms in Three Maise Inbred Lines Exhibiting Differential Sensitivity to Alachlor, *Plant Physiol*, 112, 1595–1600, 1996.

van der Zaal et al., *Plant Mol. Biol.*, 16(6), 983–998, 1991.

Kathleen A. Marrs, The Functions and Regulation of Glutathione S–Transferases in Plants, *Annu. Rev. Plant Physiol. Plant Mol. Biol.* 47, 127–158, 1996.

Sharad S. Singhal et al., Purification and Characterization of Glutathione S–Transferase from Sugarcane Leaves, *Phytochemistry*, 30, No. 5, 1409–1414, 1991.

Robert Edwards et al., Glutathione Transferases in Wheat (Triticum) Species with Activity toward Fenoxaprop–Ethyl and Other Herbicides, *Pesticide Biochemistry and Physiology*, 54, 96–104, 1996.

Czarnecka et al., *Mol. Cell. Biol.*, 8(3), 1113–1122, 1988.

Michael A. Wosnick et al., Total Chemical Synthesis and Expression in *Escherichia coli* of a Maize Glutathione–Transferase (GST) Gene, *Gene*, 76, 153–160, 1989.

Ian Jepson et al., Cloning and Characterization of Maize Herbicide Safener–induced cDNAs Encoding Subunits of Glutathione S–Transferase Isoforms I, II, and IV, *Plant Molecular Biology*, 26, 1855–1866, 1994.

Dianne A.M. van der Kop et al., Isolation and Characterization of an Auxin–Inducible Glutathione S–Transferase Gene of *Arabidopsis Thaliana*, *Plant Molecular Biology*, 30, 839–844, 1996.

Blattner et al., *Science*, 277(5331), 1453–1474, 1997.

Dilip M. Shah et al., Structural Analysis of a Maize Gene Coding for Glutathione–S–Transferase Involved in Herbicide Detoxification, *Plant Molecular Biology*, 6, 203–211, 1986.

Robert E. Moore et al., Cloning and Expression of a cDNA Encoding a Maize Glutathione–S–Transferase in E. Coli, *Nucleic Acids Research*, 14, No. 18, 7227–7235, 1986.

Kriton K. Hatzios et al., Herbicide Safeners, *J. Environ. Sci. Health*, B31(3), 545–553, 1996.

McGonigle et al., *Plant Physiol.*, 117, 332, 1998 (Abstract).

Thomas Flury et al., A 2,4–D–Inducible Glutathione S–Transferase from Soybean (Glycine Max). , *Physiologia Plantarum*, 94, 312–318, 1995.

Robert Edwards, Characterization of Glutathione Transferases and Glutathione Peroxidases in Pea, *Physiologia Plantarum*, 98, 594–604, 1996.

McGonigle, Brian et al., Hemoglutathione selectivity by soybean, Pestic. Biochem. Physiol. (1998), 62(1), 15–25.

McGonigle, Brian et al., Role of glutathione conjugation in the detoxification of sulfonylurea herbicides in plants, Book of Abstracts, 216th American Chemical Society, (1998), (Abstract).

Andrews, Nucleotide sequence of a Glutathione transferase from soybean with activity towards herbicides, *EMBL Sequence Data Library*, XP002113992.

(List continued on next page.)

Primary Examiner—Ponnathapu Achutamurthy
Assistant Examiner—Kate Kerr

(57) ABSTRACT

This invention relates to isolated nucleic acid fragments encoding all or a substantial portion of soybean (*Glycine max*) glutathione-S-transferase (GST) enzymes involved in the detoxification of xenobiotic compounds in plants and seeds; this invention further relates to isolated GST enzymes. The invention also relates to the construction of chimeric genes encoding all or a substantial portion of soybean GST enzymes, host cells transformed with those genes and methods for the recombinant production of soybean GST enzymes. Methods of constructing transgenic plants having altered levels of GST enzymes and screens for identifying soybean GST enzyme substrates and soybean GST enzyme inhibitors are also provided.

2 Claims, No Drawings

OTHER PUBLICATIONS

Skipsey, et al., Substrate and thiol specificity of a stress–inducible glutathione transferase from soybean, *FEBS Letters*, 409, pp. 370–374, 1997.

McGonigle et al., Untitled, *EMBL Sequence Data Library*, XP002113990, Jun. 1, 1998.

Ulmasov et al., The Soybean GH2/4 Gene that encodes a glutathione S–Transferase has a promoter that is activated by a wide range of chemical agents, Plant Physiology, vol. 108, No. 3, Jul. 1, 1995 pp. 919–927.

Timmerman, Molecular Characterization of Corn Glutathione S–Transferase Isozymes Involved in Herbicide Detoxication, Physiologia Plantarum, vol. 77, No. SYMP. 01, Jan. 1, 1989 pp. 465–471 XP002000778.

McGonigle et al., Pesticide Biochemistry and Physiology 62, 15–25, Homoglutathione Selectivity by Soybean Glutathione S–Transferases, 1998.

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 886 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: SE1.27B04

(xi) SEQUENCE DESCRIPTION: SEQ ID NO:1:

```
CAAACACTAC ACGTGCCATG ATCTGTCTCC ATGAGAAAGA GGTCGATTTT GAACTTGTTC     60
CGGTCAATGT GTTCGCTGCT GAGCACAAGC AGCCTCCTTT TCTCTCCAAG AATCCCTTTG    120
GTTTCATTCC AGTACTGGAA GATGGTGATC TCACTCTTTT TGAGTCCAGG GCCATTACCG    180
CATACGTGGC TGAAAAATTC AAGGAAACAG AACCCGATCT GATAAGGCAC AAGGATGCAA    240
AAGAAGCAGC ACTGGTGAAG GTATGGACAG AGGTAGAGTC TCATTACTAC GAGCCAGCAG    300
TGTCGCCCAT TATCTACGAG TACTTCGTGG CCCCTTTCCA AGGCAAAGAA CCCGACAAGT    360
CAGTGATTGA CACCAACGTT GAGAAGCTGA AGACGGTGCT TGATGTGTAC GAGGCCAAGC    420
TGAGCAGCAC CAAGTACCTT GCTGGGGACT TTTATAGCCT TGCTGATCTT AGCCATGTTT    480
CTGAAACTCA CTACTTGATG CAGACCCCTT GTGCTTCCAT GATCAATGAG CTTCCTCATG    540
TAAAGGCTTG GTGGGAGGAT ATCTCTTCTA GGCCTGCTTT CAATAAGGTT GTGGGAGGAA    600
TGAGTTTTGG TCAGAATCAT TGAGGAATGA GTGTGTTTTG TGAGGTTCAA TTACTACCTA    660
ATTTGTTGCA GTATCTAGTC AAGCAAATGT GGTGTTGGGT GTTCTTGAAA CTTGTTTCAT    720
TTCTTATAAC TAGAATTAAT TAGGAAAACG AATCAATTTT TAGAGGGGTC TTTAAGAAAA    780
AGGACTTTAA TAGTTCCTTT TGTCTTATTT GATTAATTTA AAATTTTATG TTGTAGTGTT    840
TTGATGATAT GTTTTAATAT CCTATTTCAA AAAAAAAAAA AAAAAA                   886
```

(2) INFORMATION FOR SEQ ID NO:2:

(i) SEQUENCE CHARACTERISTICS:
      (A) LENGTH: 201 amino acids

```
        (B) TYPE:  amino acid
        (C) STRANDEDNESS: Not Relevant
        (D) TOPOLOGY: Not Relevant (ii) MOLECULE TYPE:  protein (vi) ORIGINAL SOURCE:
        (F) TISSUE TYPE:  SOYBEAN (vii) IMMEDIATE SOURCE:
        (B) CLONE:  SE1.27B04

(xi) SEQUENCE DESCRIPTION: SEQ ID NO:2:

Met Ile Cys Leu His Glu Lys Glu Val Asp Phe Glu Leu Val Pro Val
1               5                  10                  15

Asn Val Phe Ala Ala Glu His Lys Gln Pro Pro Phe Leu Ser Lys Asn
            20                  25                  30

Pro Phe Gly Phe Ile Pro Val Leu Glu Asp Gly Asp Leu Thr Leu Phe
        35                  40                  45

Glu Ser Arg Ala Ile Thr Ala Tyr Val Ala Glu Lys Phe Lys Glu Thr
50                  55                  60

Glu Pro Asp Leu Ile Arg His Lys Asp Ala Lys Glu Ala Ala Leu Val
65                  70                  75                  80

Lys Val Trp Thr Glu Val Glu Ser His Tyr Tyr Glu Pro Ala Val Ser
                85                  90                  95

Pro Ile Ile Tyr Glu Tyr Phe Val Ala Pro Phe Gln Gly Lys Glu Pro
            100                 105                 110

Asp Lys Ser Val Ile Asp Thr Asn Val Glu Lys Leu Lys Thr Val Leu
        115                 120                 125

Asp Val Tyr Glu Ala Lys Leu Ser Ser Thr Lys Tyr Leu Ala Gly Asp
130                 135                 140

Phe Tyr Ser Leu Ala Asp Leu Ser His Val Ser Glu Thr His Tyr Leu
145                 150                 155                 160

Met Gln Thr Pro Cys Ala Ser Met Ile Asn Glu Leu Pro His Val Lys
                165                 170                 175

Ala Trp Trp Glu Asp Ile Ser Ser Arg Pro Ala Phe Asn Lys Val Val
            180                 185                 190

Gly Gly Met Ser Phe Gly Gln Asn His
        195                 200

(2) INFORMATION FOR SEQ ID NO:3:

(i) SEQUENCE CHARACTERISTICS:
        (A) LENGTH:  1007 base pairs
        (B) TYPE:  nucleic acid
        (C) STRANDEDNESS:  single
        (D) TOPOLOGY:  linear (ii) MOLECULE TYPE:  cDNA (iii) HYPOTHETICAL:  NO (iv) ANTI-SENSE:  NO (vi) ORIGINAL SOURCE:
        (F) TISSUE TYPE:  SOYBEAN (vii) IMMEDIATE SOURCE:
        (B) CLONE:  SSM.PK0026.G11

(xi) SEQUENCE DESCRIPTION: SEQ ID NO:3:

CACGACACTG AGCATCAGCA ATGGCAAGCG CAAGTGTTGG TAAAGAACTG ACGCTGTATT      60

CGTATTGGAG GAGCTCTTGT TCCCACCGAG TCCGAATCGC TCTCAACCTC AAAGGGCTTA    120
```

```
AATACGAATA CAAGCCCGTC AATCTGCTCA AGGGAGAACA ATCTCGCCCT GAGTTTCTCC        180

AGCTCAATCC TGTTGGTTGT GTCCCCGTTC TAGTGGATGA CCACGTTGTT CTCTATGACT        240

CTTTCGCCAT TATTATGTAT TTGGAAGATA AGTATCCTCA CAATCCTTTG CTCCCTCATG        300

ATATTTACAA GAGAGCAATC AATTTCCAGG CTGCTAGTGT TGTTTCCTCA ACAATACAAC        360

CTCTTCATAA CTTGAGTTTA CTGAACTACA TTGGGGAGAA AGTTGGCCCT GATGAAAAAC        420

TTCCTTGGGC CCAAAGTATA ATTAGAAGAG GCTTTAAAGC ACTGGAAAAG CTATTGAAAG        480

ACCACACAGG AAGATATGCA ACTGGAGATG AAGTTTTCCT GGCAGATATA TTTTTAGCAC        540

CTCAGTTACA TGCAGCATTT AAGAGATTCA ACATTCACAT GAACGAGTTC CCTATTCTAG        600

CAAGATTGCA TGAGACATAT AATGAGATCC CTGCATTCCA GGAGGCTCTG CCAGAGAACC        660

AGCCTGATGC AGTACACTAG TTGAACCAAT AATTTGGGAC AGAAATATGA GTTGATATTA        720

AGTTGGAGAA ATTGCAGCAG GAGCTACTTA TTCAGCATCC GGATGAATTC GTTGTTAAAG        780

TATTAAAATA TGATACTCAA TATAGCAATA AGGTTGCCAC ATGCAATATT TATTGCACAC        840

ATCATGTACA ATTGAAAAAA AAAAATTGGT TTCGGGTGTA TGTCTATAAA GCCTTATGTT        900

TATTTTCCAT TTCATATTCT TCCCAGAATC CCAGTCAATG TAGCTTGATG GATGATTCTT        960

AATGGTGTTT ATGGTTGAAT TGGTGTTTCA AAAAAAAAAA AAAAAAA                    1007

(2) INFORMATION FOR SEQ ID NO:4:

(i) SEQUENCE CHARACTERISTICS:
        (A) LENGTH: 219 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SSM.PK0026.G11

(xi) SEQUENCE DESCRIPTION: SEQ ID NO:4:

Met Ala Ser Ala Ser Val Gly Lys Glu Leu Thr Leu Tyr Ser Tyr Trp
1               5                   10                  15

Arg Ser Ser Cys Ser His Arg Val Arg Ile Ala Leu Asn Leu Lys Gly
                20                  25                  30

Leu Lys Tyr Glu Tyr Lys Pro Val Asn Leu Leu Lys Gly Glu Gln Ser
            35                  40                  45

Arg Pro Glu Phe Leu Gln Leu Asn Pro Val Gly Cys Val Pro Val Leu
        50                  55                  60

Val Asp His Val Val Leu Tyr Asp Ser Phe Ala Ile Ile Met Tyr
65                  70                  75                  80

Leu Glu Asp Lys Tyr Pro His Asn Pro Leu Leu Pro His Asp Ile Tyr
                85                  90                  95

Lys Arg Ala Ile Asn Phe Gln Ala Ala Ser Val Val Ser Ser Thr Ile
                100                 105                 110

Gln Pro Leu His Asn Leu Ser Leu Leu Asn Tyr Ile Gly Glu Lys Val
            115                 120                 125

Gly Pro Asp Glu Lys Leu Pro Trp Ala Gln Ser Ile Ile Arg Arg Gly
        130                 135                 140

Phe Lys Ala Leu Glu Lys Leu Leu Lys Asp His Thr Gly Arg Tyr Ala
145                 150                 155                 160
```

```
Thr Gly Asp Glu Val Phe Leu Ala Asp Ile Phe Leu Ala Pro Gln Leu
            165                 170                 175

His Ala Ala Phe Lys Arg Phe Asn Ile His Met Asn Glu Phe Pro Ile
        180                 185                 190

Leu Ala Arg Leu His Glu Thr Tyr Asn Glu Ile Pro Ala Phe Gln Glu
        195                 200                 205

Ala Leu Pro Glu Asn Gln Pro Asp Ala Val His
    210                 215
```

(2) INFORMATION FOR SEQ ID NO:5:

(i) SEQUENCE CHARACTERISTICS:
        (A) LENGTH: 902 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: GSTA (xi) SEQUENCE DESCRIPTION: SEQ ID NO:5:

```
GGCTTGACGA GGAAGTGTTA TTAGAGTTCT GGCCAAGTCC ATTTGGGATG AGGGTCAGGA    60

TTGCACTTGC TGAAAAGGGT ATCAAATATG AGTACAAAGA AGAGGACTTG AGGAACAAGA   120

GTCCTCTTCT CCTCCAAATG AACCCGGTTC ACAAGAAGAT TCCGGTTCTC ATCCACAATG   180

GCAAACCCAT TTGTGAATCC CTCATTGCTG TTCAGTACAT TGAGGAGGTT TGGAATGACA   240

GAAATCCCTT GTTGCCTTCT GACCCTTACC AGAGAGCTCA GACTAGATTC TGGGCTGATT   300

ATGTTGATAA GAAGATATAT GATCTTGGAA GGAAGATTTG GACATCAAAA GGAGAAGAAA   360

AAGAAGCTGC CAAGAAGGAG TTCATAGAAG CCCTTAAATT GTTGGAGGAA CAGCTGGGAG   420

ACAAGACTTA TTTTGGAGGA GACAATCTAG GTTTTGTGGA TATAGCGCTT GTTCCATTCT   480

ACACTTGGTT CAAAGCCTAT GAGACTTTTG GCACCCTCAA CATAGAGAGT GAGTGCCCCA   540

AGTTTATTGC TTGGGCCAAG AGGTGCCTTC AGAAAGAAAG CGTTGCCAAG TCTCTTCCTG   600

ATCAGCAAAA GGTTTATGAG TTCATTATGG ATCTAAGAAA GAAGTTAGGC ATTGAGTAGG   660

TTGGAGCTTA ATGGCCATTG TGAAGTAGTG GTTTTCCATT GGTCGTTCTT AGCCTTTCAA   720

ATAAGTAATA TTTGTGTAAT AAAAGGCACT TAGATGTGCC AAACTTCGTG CTTTCTGTAG   780

GAATGTGTGG GTTTTGGAAA ATCTCTGATG TATCTTTCAT GTGTTTGTTG GTTTTGTAAT   840

TTTTTTTTGG TATTGTCTTA TACTTGAATA ATTTGAGACT AAAAAAAAAA AAAAAAAAA    900

AA                                                                 902
```

(2) INFORMATION FOR SEQ ID NO:6:

(i) SEQUENCE CHARACTERISTICS:
        (A) LENGTH: 219 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
         (F) TISSUE TYPE: SOYBEAN (vii) IMMEDIATE SOURCE:
         (B) CLONE: GSTA (xi) SEQUENCE DESCRIPTION: SEQ ID NO:6:

Met Ser Asp Glu Val Val Leu Leu Asp Phe Trp Pro Ser Pro Phe Gly
1               5                   10                  15

Met Arg Val Arg Ile Ala Leu Ala Glu Lys Gly Ile Lys Tyr Glu Tyr
            20                  25                  30

Lys Glu Glu Asp Leu Arg Asn Lys Ser Pro Leu Leu Leu Gln Met Asn
        35                  40                  45

Pro Val His Lys Lys Ile Pro Val Leu Ile His Asn Gly Lys Pro Ile
    50                  55                  60

Cys Glu Ser Leu Ile Ala Val Gln Tyr Ile Glu Glu Val Trp Asn Asp
65                  70                  75                  80

Arg Asn Pro Leu Leu Pro Ser Asp Pro Tyr Gln Arg Ala Gln Thr Arg
                85                  90                  95

Phe Trp Ala Asp Tyr Val Asp Lys Lys Ile Tyr Asp Leu Gly Arg Lys
            100                 105                 110

Ile Trp Thr Ser Lys Gly Glu Glu Lys Glu Ala Ala Lys Lys Glu Phe
        115                 120                 125

Ile Glu Ala Leu Lys Leu Leu Glu Glu Gln Leu Gly Asp Lys Thr Tyr
130                 135                 140

Phe Gly Gly Asp Asn Leu Gly Phe Val Asp Ile Ala Leu Val Pro Phe
145                 150                 155                 160

Tyr Thr Trp Phe Lys Ala Tyr Glu Thr Phe Gly Thr Leu Asn Ile Glu
                165                 170                 175

Xaa Glu Cys Pro Lys Phe Ile Ala Trp Ala Lys Arg Cys Leu Gln Lys
            180                 185                 190

Glu Ser Val Ala Lys Ser Leu Pro Asp Gln Gln Lys Val Tyr Glu Phe
        195                 200                 205

Ile Met Asp Leu Arg Lys Lys Leu Gly Ile Glu
    210                 215

(2) INFORMATION FOR SEQ ID NO:7:

(i) SEQUENCE CHARACTERISTICS:
        (A) LENGTH: 895 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SE3.03B09

(xi) SEQUENCE DESCRIPTION: SEQ ID NO:7:

CACAACTTTG CCCCCTTGTA AAACTTCTTA TTGTGATGTC TAAAAGCGAA GACTTGAAGC    60

TTTTGGGAGG CTGGTTCAGC CCATTTGCCC TGAGGGTGCA GATTGCCCTT AACCTCAAGG    120

GTCTAGAATA TGAGGTTGTT GAAGAGACCT TGAATCCCAA AAGTGACCTG CTTCTTAAGT    180

-continued

```
CCAACCCTGT GCACAAGAAA ATCCCAGTTT TCTTCCATGG AGATAAAGTC ATTTGTGAAT      240

CTGCAATCAT AGTTGAGTAC ATTGATGAGG CTTGGACTAA TGTTCCCTCC ATCCTTCCAC      300

AAAATGCTTA TGATCGTGCT AATGCTCGAT TTTGGTTTGC CTACATTGAT GAGAAGTGGT      360

TTACGTCCTT GAGAAGTGTT CTAGTGGCTG AAGATGATGA GGCAAAGAAG CCACACTTTG      420

AGCAAGCAGA AGAAGGGCTT GAGAGGTTGG AAGAAGTGTT CAACAAGTAC AGTGAAGGGA      480

AGGCCTATTT CGGAGGAGAT AGCATTGGAT TCATTGACAT TGGTTTTGGG AGCTTCTTGA      540

GTTGGATGAG AGTCATAGAG GAGATGAGTG GAAGAAAATT GCTTGATGAA AGAAGCACC       600

CTGGTTTGAC CCAATGGGCT GAAACGTTTG CTGCTGATCC TGCTGTGAAG GGCATTCTTC      660

CAGAGACTGA TAAGCTTGTT GAGTTTGCCA AGATTCTTCA GCTAAAATGG ACTGCTGCAG      720

CAGCTGCAGC TGCAAAGTAA ATGGAATCAA ATTAATTGCG AGAGTATTTT CAAAATTGTT      780

GTCCAAGTTG TTTTTATCTC AGGCTATGTT GTTGCAACTT TATTTATTTA AAAGTTATTT      840

TAAATTTAAA ATGTAAAATA TTAAGAAAGT TTAAGTAAGT TAGTTGAAAA ATTTT           895
```

(2) INFORMATION FOR SEQ ID NO:8:

(i) SEQUENCE CHARACTERISTICS:
        (A) LENGTH: 234 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SE3.03B09

(xi) SEQUENCE DESCRIPTION: SEQ ID NO:8:

```
Met Ser Lys Ser Glu Asp Leu Lys Leu Leu Gly Gly Trp Phe Ser Pro
1               5                   10                  15

Phe Ala Leu Arg Val Gln Ile Ala Leu Asn Leu Lys Gly Leu Glu Tyr
                20                  25                  30

Glu Val Val Glu Glu Thr Leu Asn Pro Lys Ser Asp Leu Leu Leu Lys
            35                  40                  45

Ser Asn Pro Val His Lys Lys Ile Pro Val Phe Phe His Gly Asp Lys
        50                  55                  60

Val Ile Cys Glu Ser Ala Ile Ile Val Glu Tyr Ile Asp Glu Ala Trp
65                  70                  75                  80

Thr Asn Val Pro Ser Ile Leu Pro Gln Asn Ala Tyr Asp Arg Ala Asn
                85                  90                  95

Ala Arg Phe Trp Phe Ala Tyr Ile Asp Glu Lys Trp Phe Thr Ser Leu
            100                 105                 110

Arg Ser Val Leu Val Ala Glu Asp Asp Glu Ala Lys Lys Pro His Phe
        115                 120                 125

Glu Gln Ala Glu Glu Gly Leu Glu Arg Leu Glu Val Phe Asn Lys
    130                 135                 140

Tyr Ser Glu Gly Lys Ala Tyr Phe Gly Gly Asp Ser Ile Gly Phe Ile
145                 150                 155                 160

Asp Ile Gly Phe Gly Ser Phe Leu Ser Trp Met Arg Val Ile Glu Glu
                165                 170                 175

Met Ser Gly Arg Lys Leu Leu Asp Glu Lys Lys His Pro Gly Leu Thr
            180                 185                 190
```

Gln Trp Ala Glu Thr Phe Ala Ala Asp Pro Ala Val Lys Gly Ile Leu
    195                 200                 205

Pro Glu Thr Asp Lys Leu Val Glu Phe Ala Lys Ile Leu Gln Leu Lys
    210                 215                 220

Trp Thr Ala Ala Ala Ala Ala Ala Lys
225                 230

(2) INFORMATION FOR SEQ ID NO:9:

(i) SEQUENCE CHARACTERISTICS:
        (A) LENGTH:  931 base pairs
        (B) TYPE:  nucleic acid
        (C) STRANDEDNESS:  single
        (D) TOPOLOGY:  linear (ii) MOLECULE TYPE:  cDNA (iii) HYPOTHETICAL:  NO (iv) ANTI-SENSE:  NO (vi) ORIGINAL SOURCE:
        (F) TISSUE TYPE:  SOYBEAN (vii) IMMEDIATE SOURCE:
        (B) CLONE:  SE6.PK0037.H4

(xi) SEQUENCE DESCRIPTION:  SEQ ID NO:9:

```
CTGCAGGTAG TTTTTCTGTT TGAAGTGCTA CAAACAATGG CAGCTACTCA GGAAGATGTG     60

ACGCTTTTGG GAGTTGTTGG AAGCCCGTTT GTGTGCAGGG TCCAGATTGC CCTCAAATTG    120

AAGGGAATTG AATGCAAATT TTTGGAAGAA AATTTGGCAA ACAAGAGTGA TCTACTTCTC    180

AAATCCAACC CCGTTTACAA GAAGGTTCCA GTGTTTATTC ATAATGAGAA GCCCATAGCA    240

GAGTCTCTTG TGATTGTTGA GTACATTGAT GAGACATGGA AGAACAACCC CATCTTGCCT    300

TCTGATCCTT ACCAAAGATC CTTTGCTCGG TTTTGGTCCA AGTTCATAGA TGACAAGATT    360

GTGGGTGCTT CATGGAAATC TGTTTTCACG GTTGATGAGA AGAGCGTGA GAAGAATGTT    420

GAAGAATCGT TGGAGGCTCT GCAGTTTCTT GAGAATGAAC TACAGGACAA AAGGTTCTTT    480

GGAGGAGATG AATTTGGATT TGTAGATATT GCTGGTGTCT TCATTGCATT TTCAATCCCA    540

ATTTTCCAAG AAGTAGCAGG GTTGCAATTA TTCACCAGTG AGAAATTTCC TAAGCTCTTC    600

AAATGGAGCC AAGAGTTGAT CAACCACCCT GTTGTCAAAG ATGTCCTTCC TCCTAGAGAA    660

CCACTTTTTG CCTTCTTCAA ATCCCTCTAT GAAAGCCTTT CTGCTTCAAA ATAGATTGTT    720

TAAGAATGAT TGTGTGAACT ACTTGTCGCT CATTGAATTA TTGTTGTTTG AATTTCATGT    780

CAATTTGATA CTATATGTAA TTTAGTAACC TGGGATATTA GGATATCCCC AAGGAACAAA    840

GAATCCTAGG ATTTTGTTTC CATTTTGGCC ATTTCAGTTA ATAATTAAAG AAACTCTATT    900

TTTTCTTGTT ACAAAAAAAA AAAAAAAAA A                                    931
```

(2) INFORMATION FOR SEQ ID NO:10:

(i) SEQUENCE CHARACTERISTICS:
        (A) LENGTH:  225 amino acids
        (B) TYPE:  amino acid
        (C) STRANDEDNESS: Not Relevant
        (D) TOPOLOGY: Not Relevant (ii) MOLECULE TYPE:  protein (vi) ORIGINAL SOURCE:
        (F) TISSUE TYPE:  SOYBEAN (vii) IMMEDIATE SOURCE:

(B) CLONE: SE6.PK0037.H4

(xi) SEQUENCE DESCRIPTION: SEQ ID NO:10:

```
Met Ala Ala Thr Gln Glu Asp Val Thr Leu Leu Gly Val Val Gly Ser
1               5                  10                 15

Pro Phe Val Cys Arg Val Gln Ile Ala Leu Lys Leu Lys Gly Ile Glu
            20                  25                 30

Cys Lys Phe Leu Glu Glu Asn Leu Ala Asn Lys Ser Asp Leu Leu Leu
        35                  40                 45

Lys Ser Asn Pro Val Tyr Lys Lys Val Pro Val Phe Ile His Asn Glu
    50                  55                  60

Lys Pro Ile Ala Glu Ser Leu Val Ile Val Glu Tyr Ile Asp Glu Thr
65                  70                  75                  80

Trp Lys Asn Asn Pro Ile Leu Pro Ser Asp Pro Tyr Gln Arg Ser Phe
                85                  90                  95

Ala Arg Phe Trp Ser Lys Phe Ile Asp Asp Lys Ile Val Gly Ala Ser
            100                 105                110

Trp Lys Ser Val Phe Thr Val Asp Glu Lys Glu Arg Glu Lys Asn Val
        115                 120                 125

Glu Glu Ser Leu Glu Ala Leu Gln Phe Leu Glu Asn Glu Leu Gln Asp
130                 135                 140

Lys Arg Phe Phe Gly Gly Asp Glu Phe Gly Phe Val Asp Ile Ala Gly
145                 150                 155                 160

Val Phe Ile Ala Phe Ser Ile Pro Ile Phe Gln Glu Val Ala Gly Leu
                165                 170                 175

Gln Leu Phe Thr Ser Glu Lys Phe Pro Lys Leu Phe Lys Trp Ser Gln
            180                 185                 190

Glu Leu Ile Asn His Pro Val Val Lys Asp Val Leu Pro Pro Arg Glu
            195                 200                 205

Pro Leu Phe Ala Phe Phe Lys Ser Leu Tyr Glu Ser Leu Ser Ala Ser
        210                 215                 220

Lys
225
```

(2) INFORMATION FOR SEQ ID NO:11:

(i) SEQUENCE CHARACTERISTICS:
        (A) LENGTH: 946 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SE6.PK0048.D7

(xi) SEQUENCE DESCRIPTION: SEQ ID NO:11:

```
TTGCACTACA AATCAGTTTT CTACTTGAAT CTTCGTTATC CTTCTTTTTT TCTCCTTGAA     60

CTCGAATATT CACTATGGCA GATGAGGTGG TTCTGCTAGA TTTCTGGCCA AGTCCATTTG    120

GGATGAGGGT CAGGATTGCA CTTGCTGAAA AGGGTATCAA ATATGAGTCC AAAGAAGAGG    180

ACTTGCAGAA CAAGAGCCCT TTGCTCCTCA AAATGAACCC GGTTCACAAG AAAATCCCGG    240
```

```
TTCTCATCCA CAATGGCAAA CCCATTTGTG AATCTCTCGT TGCTGTTCAG TACATTGAGG      300

AGGTCTGGAA TGACAGAAAT CCCTTGTTGC CTTCTGACCC TTACCAGAGA GCTCAGGCTA      360

GATTCTGGGC TGACTTTGTT GACAATAAGA TATTTGATCT TGGAAGAAAG ATTTGGACAT      420

CAAAGGGAGA AGAAAAAGAA GCTGCCAAAA AGGAGTTCAT AGAGGCCCTT AAATTATTGG      480

AGGAACAGCT GGGAGACAAG ACTTATTTTG GAGGAGACGA TCTAGGTTTT GTGGATATAG      540

CACTTATTCC ATTCGACACT TGGTTCAAGA CTTTTGGCAG CCTCAACATA GAGAGTGAGT      600

GCCCCAAGTT TGTTGCTTGG GCCAAGAGGT GCCTGCAGAA AGACAGTGTT GCCAAGTCTC      660

TTCCTGATCA ACACAAGGTC TATGAGTTCA TTATGGACAT AAGAAAGAAG TTCGACATTG      720

AGTAGGTTCA TGTTGGATTT TAATAGCCAT AGTGACGTAT TGATCATTCT TGGCCTTTCA      780

ACTAAATAGT ATTTGTGTAG TAAATTAAAG GCACTTGGAT GTACCAAACT TCATGCTTTT      840

TGTAGGAGTG CGTAGGTTTT AAAAATTTTC TGATGTATCT TTCATGTGTT TGTTGGTTTT      900

GTAACAGAAT ATTTCCTATA TTATACATAA AAAAAAAAAA AAAAAA                    946

(2) INFORMATION FOR SEQ ID NO:12:

(i) SEQUENCE CHARACTERISTICS:
        (A) LENGTH: 216 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
         (F) TISSUE TYPE: SOYBEAN (vii) IMMEDIATE SOURCE:
          (B) CLONE: SE6.PK0048.D7

(xi) SEQUENCE DESCRIPTION: SEQ ID NO:12:

Met Ala Asp Glu Val Val Leu Leu Asp Phe Trp Pro Ser Pro Phe Gly
1               5                  10                  15

Met Arg Val Arg Ile Ala Leu Ala Glu Lys Gly Ile Lys Tyr Glu Ser
                20                  25                  30

Lys Glu Glu Asp Leu Gln Asn Lys Ser Pro Leu Leu Leu Lys Met Asn
            35                  40                  45

Pro Val His Lys Lys Ile Pro Val Leu Ile His Asn Gly Lys Pro Ile
        50                  55                  60

Cys Glu Ser Leu Val Ala Val Gln Tyr Ile Glu Glu Val Trp Asn Asp
65                  70                  75                  80

Arg Asn Pro Leu Leu Pro Ser Asp Pro Tyr Gln Arg Ala Gln Ala Arg
                85                  90                  95

Phe Trp Ala Asp Phe Val Asp Asn Lys Ile Phe Asp Leu Gly Arg Lys
            100                 105                 110

Ile Trp Thr Ser Lys Gly Glu Glu Lys Glu Ala Ala Lys Lys Glu Phe
        115                 120                 125

Ile Glu Ala Leu Lys Leu Leu Glu Glu Gln Leu Gly Asp Lys Thr Tyr
    130                 135                 140

Phe Gly Gly Asp Asp Leu Gly Phe Val Asp Ile Ala Leu Ile Pro Phe
145                 150                 155                 160

Asp Thr Trp Phe Lys Thr Phe Gly Ser Leu Asn Ile Glu Ser Glu Cys
                165                 170                 175

Pro Lys Phe Val Ala Trp Ala Lys Arg Cys Leu Gln Lys Asp Ser Val
            180                 185                 190
```

```
Ala Lys Ser Leu Pro Asp Gln His Lys Val Tyr Glu Phe Ile Met Asp
    195                 200                 205

Ile Arg Lys Lys Phe Asp Ile Glu
    210                 215
```

(2) INFORMATION FOR SEQ ID NO:13:

(i) SEQUENCE CHARACTERISTICS:
        (A) LENGTH: 977 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SES8W.PK0028.C6

(xi) SEQUENCE DESCRIPTION: SEQ ID NO:13:

```
CTGATTCCCG GCTCAATAAG AGGAGAATAC CTTAGGAATC CATAAGAAAC ATTAATTCAC    60

CACTATAGTT GTTCTGTTAG AAGTGCTACA AACAACAATG GCTGCTAATC AGGAAGATGT   120

GAAGCTTTTG GGAGCTACTG GAAGCCCATT TGTGTGCAGG GTTCAGATTG CCCTCAAGTT   180

GAAGGGAGTT CAATACAAAT TTTTGGAAGA AAATTTGAGG AACAAGAGTG AACTGCTTCT   240

CAAATCCAAC CCAGTTCACA GAAGGTTCC AGTGTTTATT CACAATGAGA AGCCCATAGC    300

AGAGTCTCTT GTGATTGTTG AATACATTGA TGAGACATGG AAGAACAACC CCATCTTGCC   360

TTCTGATCCT TACCAAAGAG CCTTGGCTCG TTTCTGGTCC AAATTCATTG ATGACAAGGT   420

TGTGGGTGCT GCATGGAAAT ATATTTATAC TGTTGATGAG AAAGAGCGTG AGAAGAATGT   480

TGAAGAGTCA TATGAGGCTC TGCAGTTTCT TGAGAATGAG CTGAAGGACA GAAGTTTTT    540

TGGAGGAGAG GAAATTGGGT TGGTAGATAT TGCTGCTGTC TTCATAGCAT TTTGGATCCC   600

TATAATTCAA GAAGTATTGG GTTTGAAGTT ATTCACAAGT GAGAAATTTC CTAAGCTCTA   660

CAAATGGAGC CAAGAGTTCA TCAACCACCC TGTTGTCAAA CAAGTCCTTC CTCCTAGAGA   720

TCAACTTTTT GCCTTCTACA AAGCCTGCCA TGAAAGTCTT TCTGCTTCAA AATAGACTTA   780

TTTAAGGATA GTTGTGTGAA CTACTGGTCT CTCATTTGTG AGTTATTGCA GTTTGAATTT   840

CATGTCAATT TGGTTTTATA TGTAATTTAG TAACCTGGGA TATCTCCCAT GGAGAAAATA   900

ATCCTTGGAT CTTGTTTCCA TTTTGGCCAT TTCAGTTAAT AAAGAAATTC ATTTTTTCCA   960

AAAAAAAAAA AAAAAA                                                    977
```

(2) INFORMATION FOR SEQ ID NO:14:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:

(B) CLONE: SES8W.PK0028.C6

(xi) SEQUENCE DESCRIPTION: SEQ ID NO:14:

Met Ala Ala Asn Gln Glu Asp Val Lys Leu Leu Gly Ala Thr Gly Ser
1               5                  10                  15

Pro Phe Val Cys Arg Val Gln Ile Ala Leu Lys Leu Lys Gly Val Gln
                20                  25                  30

Tyr Lys Phe Leu Glu Glu Asn Leu Arg Asn Lys Ser Glu Leu Leu Leu
            35                  40                  45

Lys Ser Asn Pro Val His Lys Lys Val Pro Val Phe Ile His Asn Glu
    50                  55                  60

Lys Pro Ile Ala Glu Ser Leu Val Ile Val Glu Tyr Ile Asp Glu Thr
65                  70                  75                  80

Trp Lys Asn Asn Pro Ile Leu Pro Ser Asp Pro Tyr Gln Arg Ala Leu
                85                  90                  95

Ala Arg Phe Trp Ser Lys Phe Ile Asp Asp Lys Val Val Gly Ala Ala
            100                 105                 110

Trp Lys Tyr Ile Tyr Thr Val Asp Glu Lys Glu Arg Glu Lys Asn Val
        115                 120                 125

Glu Glu Ser Tyr Glu Ala Leu Gln Phe Leu Glu Asn Glu Leu Lys Asp
130                 135                 140

Lys Lys Phe Phe Gly Gly Glu Glu Ile Gly Leu Val Asp Ile Ala Ala
145                 150                 155                 160

Val Phe Ile Ala Phe Trp Ile Pro Ile Ile Gln Glu Val Leu Gly Leu
                165                 170                 175

Lys Leu Phe Thr Ser Glu Lys Phe Pro Lys Leu Tyr Lys Trp Ser Gln
            180                 185                 190

Glu Phe Ile Asn His Pro Val Val Lys Gln Val Leu Pro Pro Arg Asp
        195                 200                 205

Gln Leu Phe Ala Phe Tyr Lys Ala Cys His Glu Ser Leu Ser Ala Ser
    210                 215                 220

Lys
225

(2) INFORMATION FOR SEQ ID NO:15:

(i) SEQUENCE CHARACTERISTICS:
        (A) LENGTH: 1006 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SR1.PK0011.D6

(xi) SEQUENCE DESCRIPTION: SEQ ID NO:15:

ATAGTGCTGC AATGGCTTCA AGTCAGGAGG AGGTGACCCT TTTGGGAGCT ACTGGAAGCC      60

CATTTGTGTG CAGGGTTCAT ATTGCCCTCA AGTTGAAGGG AGTTCAATAC AAATATGTCG     120

AAGAAAATTT GAGGAACAAG AGTGAACTGC TTCTCAAATC CAACCCAGTT CACAAGAAGG     180

TTCCAGTGTT TATTCACAAT GAGAAGCCCA TAGCAGAGTC TCTTGTGATT GTTGAATACA     240

-continued

```
TTGATGAGAC ATGGAAGAAC AACCCCATCT TGCCTTCTGA TCCTTACCAA AGAGCCTTGG      300

CTCGTTTCTG GTCCAAATTC ATTGATGATA AGGTTTTTGG TGCTGCATGG AAATCCGTTT      360

TCACAGCTGA TGAGAAAGAG CGTGAGAAGA ATGTTGAGGA AGCAATTGAG CTCTGCAGTT      420

TCTTGAGAAT GAGATAAAGG ACAAGAAGTT CTTTGGAGGA GAGGAGATTG GGTTGGTAGA      480

TATTGCTGCT GTCTACATAG CATTTTGGGT CCCTATGGTT CAAGAAATTG CAGGGTTGGA      540

GTTATTCACA AGTGAGAAAT TCCTAAGCT CCACAATTGG AGCCAAGAAT TTTTGAACCA       600

TCCAATTGTC AAAGAAAGTC TGCCCCCTAG AGATCCTGTT TTCTCCTTTT TCAAGGGTCT      660

CTATGAAAGC CTTTTTGGTT CAAAATAGAT TTGATGATGT GGTGTGAGAC TTAGTATTTC      720

TAAGAATTAT GTGTTTGTTA AAGGCTTCTA TGAAAGCCTC ACTGCTTCAA AATAGATTCA      780

TGTATGTGAG ACTCAGAATC TCTGGGGAAA ATTGTGTGTG GTGTGGACTA CTTGTTTTGT      840

TTGTCATTGA GCTATATCGC TGTTAATTAG GATTTTGTTT CAAAATGATG CTTATAAGTT      900

GTAATCTAGG ATTTCTCCCT TTGAAATCCT AGGTTGTTCT TGACATTTGC TATTTCAAAG      960

AATAAATATA TAGCATCTTT CTATTTCTCA AAAAAAAAAA AAAAAA                    1006
```

(2) INFORMATION FOR SEQ ID NO:16:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SR1.PK0011.D6

(xi) SEQUENCE DESCRIPTION: SEQ ID NO:16:

```
Met Ala Ser Ser Gln Glu Glu Val Thr Leu Leu Gly Ala Thr Gly Ser
  1               5                  10                  15

Pro Phe Val Cys Arg Val His Ile Ala Leu Lys Leu Lys Gly Val Gln
                 20                  25                  30

Tyr Lys Tyr Val Glu Glu Asn Leu Arg Asn Lys Ser Glu Leu Leu Leu
             35                  40                  45

Lys Ser Asn Pro Val His Lys Val Pro Val Phe Ile His Asn Glu
 50                  55                  60

Lys Pro Ile Ala Glu Ser Leu Val Ile Val Glu Tyr Ile Asp Glu Thr
 65                  70                  75                  80

Trp Lys Asn Asn Pro Ile Leu Pro Ser Asp Pro Tyr Gln Arg Ala Leu
                 85                  90                  95

Ala Arg Phe Trp Ser Lys Phe Ile Asp Asp Lys Val Phe Gly Ala Ala
                100                 105                 110

Trp Lys Ser Val Phe Thr Ala Asp Glu Lys Glu Arg Glu Lys Asn Val
            115                 120                 125

Glu Glu Ala Ile Glu Ala Leu Gln Phe Leu Glu Asn Glu Ile Lys Asp
        130                 135                 140

Lys Lys Phe Phe Gly Gly Glu Glu Ile Gly Leu Val Asp Ile Ala Ala
145                 150                 155                 160

Val Tyr Ile Ala Phe Trp Val Pro Met Val Gln Glu Ile Ala Gly Leu
                165                 170                 175

Glu Leu Phe Thr Ser Glu Lys Phe Pro Lys Leu His Asn Trp Ser Gln
```

```
                  180               185               190
Glu Phe Leu Asn His Pro Ile Val Lys Glu Ser Leu Pro Pro Arg Asp
            195               200               205
Pro Val Phe Ser Phe Phe Lys Gly Leu Tyr Glu Ser Leu Phe Gly Ser
    210               215               220
Lys
225
```

(2) INFORMATION FOR SEQ ID NO:17:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SS1.PK0002.F7

(xi) SEQUENCE DESCRIPTION: SEQ ID NO:17:

```
AGCTAGTTCA CAGCTTCAGT TCGTTTTTGT TGATCCTGTG AACTTATGGC TGACGGGGTG    60
GTTCTGTTGG ATACATGGGC CAGCATGTTT GGGATGAGGG TTAGGATTGC ATTAGCTGAA   120
AAGGGTGTTG AGTATGAATA CAAGGAAGAA AATCTCAGGA CAAGAGTCC TTTGCTTTTG   180
CAAATGAACC CAATTCACAA GAAAATTCCA GTTCTGATCC ATAATGGCAA ACCAATTTGT   240
GAATCTGCAA TTATAGTGCA GTACATTGAT GAGGTCTGGA ATGATAAAGC TCCAATCTTG   300
CCCTCTGACC CTTATGAGAG AGCTCAAGCC AGATTCTGGG TAGATTACAT TGACAAAAAG   360
GTGTATGACA CTTGGAGGAA AATGTGGCTT TCTAAAGGAG AGGAGCATGA GGCAGGGAAG   420
AAGGAGTTTA TCTCTATCTT TAAGCAGCTA GAAGAGACAC TGAGTGACAA AGCTTATTAT   480
GGAAGTGACA CCTTTGGGTT CCTTGATATT GGTTTGATCC CTTTCTACAG TTGGTTTTAT   540
ACCTTTGAGA CATATGGTAA CTTCAAAATG GAAGAAGAGT GTCCTAAACT CGTTGCTTGG   600
GCTAAGAGAT GCATGCAAAG AGAGGCTGTG TCCAAATCTC TTTCCTGATG AGAAGAAGGT   660
GTATGACTAT GTTGTGGCCG TAACAAAATT ACTTGAGTCA AACTAGAGAG ACTTCTTGAA   720
TAAATTCACG TAAGGTCTTG TGTAATTTTT ATCTTATGTT TGCTTGGGAG TTACTTATAG   780
CTTCCTAGAC ACTTGAGTGT GTCTAGTGTC TGCAGGATTT GTAACTTTAT CTTATGTTTG   840
CTAGCCTTCA GTTACTTATG ATTGCTAGAC CCTTGAGTGT GTCTACAGGA TTTGGAGCTG   900
AGGAAGGATG GATGTTGTAA TGTTTGTTTT AAGTTGTGTG TTTATGATCA ATAAATCACT   960
CATTTTATAA GGACAAAAAA AAAAAAAAA AAA                                 993
```

(2) INFORMATION FOR SEQ ID NO:18:

(i) SEQUENCE CHARACTERISTICS:
        (A) LENGTH: 200 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
    (F) TISSUE TYPE: SOYBEAN (vii) IMMEDIATE SOURCE:
    (B) CLONE: SS1.PK0002.F7

(xi) SEQUENCE DESCRIPTION: SEQ ID NO:18:

```
Met Ala Asp Gly Val Val Leu Leu Asp Thr Trp Ala Ser Met Phe Gly
1               5                   10                  15

Met Arg Val Arg Ile Ala Leu Ala Glu Lys Gly Val Glu Tyr Glu Tyr
                20                  25                  30

Lys Glu Glu Asn Leu Arg Asn Lys Ser Pro Leu Leu Leu Gln Met Asn
            35                  40                  45

Pro Ile His Lys Lys Ile Pro Val Leu Ile His Asn Gly Lys Pro Ile
        50                  55                  60

Cys Glu Ser Ala Ile Ile Val Gln Tyr Ile Asp Glu Val Trp Asn Asp
65                  70                  75                  80

Lys Ala Pro Ile Leu Pro Ser Asp Pro Tyr Glu Arg Ala Gln Ala Arg
                85                  90                  95

Phe Trp Val Asp Tyr Ile Asp Lys Lys Val Tyr Asp Thr Trp Arg Lys
                100                 105                 110

Met Trp Leu Ser Lys Gly Glu Glu His Glu Ala Gly Lys Lys Glu Phe
            115                 120                 125

Ile Ser Ile Phe Lys Gln Leu Glu Glu Thr Leu Ser Asp Lys Ala Tyr
130                 135                 140

Tyr Gly Ser Asp Thr Phe Gly Phe Leu Asp Ile Gly Leu Ile Pro Phe
145                 150                 155                 160

Tyr Ser Trp Phe Tyr Thr Phe Glu Thr Tyr Gly Asn Phe Lys Met Glu
                165                 170                 175

Glu Glu Cys Pro Lys Leu Val Ala Trp Ala Lys Arg Cys Met Gln Arg
            180                 185                 190

Glu Ala Val Ser Lys Ser Leu Ser
            195                 200
```

(2) INFORMATION FOR SEQ ID NO:19:

(i) SEQUENCE CHARACTERISTICS:
       (A) LENGTH: 935 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (F) TISSUE TYPE: SOYBEAN (vii) IMMEDIATE SOURCE:
       (B) CLONE: SS1.PK0005.E6

(xi) SEQUENCE DESCRIPTION: SEQ ID NO:19:

```
ATTTTCTTCA TCCTTCTCTG TTCTCCTAGA ACTTGATTAC TTGAACATTC CCTATGACAG      60

ATGAGGTGGT TCTTCTGGAT TTCTGGCCAA GTCCATTTGG GATGAGGGTC AGGATTGCAC     120

TTGCTGAAAA GGGTATCGAA TATGAGTACA AGAAGAGGA CTTGAGGAAC AAGAGTCCTC     180

TTCTCTTACA AATGAACCCG GTTCACAAGA AGATTCCGGT TCTCATCCAC AATGGCAAAC     240

CCATTTCCGA ATCCCTCATT GCTGTTCAGT ACATTGAGGA GGTTTGGAAT GACAGAAATC     300
```

```
CCTTGTTGCC TTCAGACCCT TACCAGAGAG CTCAGGCTAG ATTCTGGGCT GATTATGTTG      360
ACATTAAGAT ACATGATCTT GGAAAGAAAT TTGGACATCA AAGGGAGAAG AAAAAGAAGC      420
TGCCAAGAAG GAGTTCATAG AGGCCCTTAA ATTGTTGGAG AACAGCTGG GAGATAAGAC       480
TTATTTTGGA GGAGACAATA TTGGTTTTGT GGATATAGCA CTTGTTCCAT TCTACACTTG      540
GTTCAAAGTC TATGAGACTT TTGGCAGCCT CAACATTGAG AATGAGTGCC CCAGGTTTGT      600
TGCTTGGGCC AAGAGGTGCC TACAGAAAGA GAGTGTTGCA AAGTCTCTTC CTGATCAGCA      660
CAAGGTCTAT GAGTTCGTTG TGGAGATAAG AAAGAAGTTA GTCATCGAGT AGGTTTCATG      720
TTGGATCTTA ATAGCCATAG TGAAGTATTG GTCGTTCTTG ACCTTTCAAC TAAATAATAT      780
TTGTGTAATA AAAAGGCATT TGGATGTGCC AAACTTCATG CTTTCTGTTG GATTGTGTAG      840
GTTTTAAAAT TTTTCTGATG TATCTTTCAT GTGTTTGTTG GTTTTGCAAT AGAGTATTTT      900
CCGTATTATC ATATAAAAAA AAAAAAAAAA AAAA                                  935
```

(2) INFORMATION FOR SEQ ID NO:20:

(i) SEQUENCE CHARACTERISTICS:
        (A) LENGTH: 219 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SS1.PK0005.E6

(xi) SEQUENCE DESCRIPTION: SEQ ID NO:20:

```
Met Thr Asp Glu Val Val Leu Leu Asp Phe Trp Pro Ser Pro Phe Gly
 1               5                  10                  15

Met Arg Val Arg Ile Ala Leu Ala Glu Lys Gly Ile Glu Tyr Glu Tyr
            20                  25                  30

Lys Glu Glu Asp Leu Arg Asn Lys Ser Pro Leu Leu Leu Gln Met Asn
        35                  40                  45

Pro Val His Lys Lys Ile Pro Val Leu Ile His Asn Gly Lys Pro Ile
    50                  55                  60

Ser Glu Ser Leu Ile Ala Val Gln Tyr Ile Glu Glu Val Trp Asn Asp
65                  70                  75                  80

Arg Asn Pro Leu Leu Pro Ser Asp Pro Tyr Gln Arg Ala Gln Ala Arg
                85                  90                  95

Phe Trp Ala Asp Tyr Val Asp Ile Lys Ile His Asp Leu Gly Lys Lys
            100                 105                 110

Ile Trp Thr Ser Lys Gly Glu Glu Lys Glu Ala Ala Lys Lys Glu Phe
        115                 120                 125

Ile Glu Ala Leu Lys Leu Leu Glu Glu Gln Leu Gly Asp Lys Thr Tyr
    130                 135                 140

Phe Gly Gly Asp Asn Ile Gly Phe Val Asp Ile Ala Leu Val Pro Phe
145                 150                 155                 160

Tyr Thr Trp Phe Lys Val Tyr Glu Thr Phe Gly Ser Leu Asn Ile Glu
                165                 170                 175

Asn Glu Cys Pro Arg Phe Val Ala Trp Ala Lys Arg Cys Leu Gln Lys
            180                 185                 190

Glu Ser Val Ala Lys Ser Leu Pro Asp Gln His Lys Val Tyr Glu Phe
```

```
                195                 200                 205
Val Val Glu Ile Arg Lys Lys Leu Val Ile Glu
    210                 215
```

(2) INFORMATION FOR SEQ ID NO:21:

(i) SEQUENCE CHARACTERISTICS:
        (A) LENGTH: 895 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SS1.PK0014.A1

(xi) SEQUENCE DESCRIPTION: SEQ ID NO:21:

```
AAATAAGTAT CTTCGTAGTT GCATAAGTCA AGAGAAGAAG TGAAGTGGCT GCAATGGCTT    60
CAAGTCAGGA AGAGGTGACC CTTTTGGGAG TTGTGGGAAG CCCATTTCTA CACAGGGTTC   120
AGATTGCTCT CAAGTTGAAG GGAGTTGAAT ACAAATATTT GGAAGACGAT TTGAACAACA   180
AGAGTGATTT GCTCCTCAAG TATAACCCAG TTTACAAAAT GATTCCAGTG CTTGTTCACA   240
ATGAGAAGCC CATTTCAGAG TCCCTTGTGA TTGTTGAGTA CATTGATGAC ACATGGAAAA   300
ACAATCCCAT CTTGCCTTCT GATCCCTACC AAAGAGCCTT GGCTCGTTTC TGGGCTAAGT   360
TCATTGATGA CAAGTGTGTG GTTCCAGCAT GGAAATCTGC TTTTATGACT GATGAGAAAG   420
AGAAAGAGAA GGCTAAAGAA GAGTTATTTG AGGCTCGAG TTTTCTTGAG AATGAGTTGA   480
```

```
Pro Phe Leu His Arg Val Gln Ile Ala Leu Lys Leu Lys Gly Val Glu
         20                  25                  30

Tyr Lys Tyr Leu Glu Asp Asp Leu Asn Asn Lys Ser Asp Leu Leu Leu
         35                  40                  45

Lys Tyr Asn Pro Val Tyr Lys Met Ile Pro Val Leu Val His Asn Glu
 50                  55                  60

Lys Pro Ile Ser Glu Ser Leu Val Ile Val Glu Tyr Ile Asp Asp Thr
 65                  70                  75                  80

Trp Lys Asn Asn Pro Ile Leu Pro Ser Asp Pro Tyr Gln Arg Ala Leu
             85                  90                  95

Ala Arg Phe Trp Ala Lys Phe Ile Asp Asp Lys Cys Val Val Pro Ala
             100                 105                 110

Trp Lys Ser Ala Phe Met Thr Asp Glu Lys Glu Lys Glu Lys Ala Lys
             115                 120                 125

Glu Glu Leu Phe Glu Ala Leu Ser Phe Leu Glu Asn Glu Leu Lys Gly
     130                 135                 140

Lys Phe Gly Gly Glu Glu Phe Gly Phe Val Asp Ile Ala Ala Val
145                 150                 155                 160

Leu Ile Pro Ile Ile Gln Glu Ile Ala Gly Leu Gln Leu Phe Thr Ser
             165                 170                 175

Glu Lys Phe Pro Lys Leu Ser Lys Trp Ser Gln Asp Phe His Asn His
             180                 185                 190

Pro Val Val Asn Glu Val Met Pro Pro Lys Asp Gln Leu Phe Ala Tyr
             195                 200                 205

Phe Lys Ala Arg Ala Gln Ser Phe Val Ala Lys Arg Lys Asn
 210                 215                 220
```

(2) INFORMATION FOR SEQ ID NO:23:

(i) SEQUENCE CHARACTERISTICS:
        (A) LENGTH: 885 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: SOYBEAN (vii) IMMEDIATE SOURCE:
        (B) CLONE: SS1.PK0020.B10

(xi) SEQUENCE DESCRIPTION: SEQ ID NO:23:

```
CCATAGCAAT GGCAGAGCAA GACAAGGTGA TCCTACACGG GATGTGGGCC AGCCCTTATG    60

CCAAGAGGGT GGAATTGGCC CTTAATTTTA AGGGCATACC CTATGAGTAT GTTGAAGAAG   120

ACTTGAGAAA TAAGAGTGAT TTGCTTCTAA AGTACAACCC TGTTCACAAG AAGGTTCCTG   180

TACTTGTTCA TAATGGAAAG GCCATTGCTG AATCCATGGT GATCCTTGAG TATATTGATG   240

AAACATGGAA AGATGGTCCT AAACTGCTTC CAAGTGATTC TTACAAACGA GCCCAAGCTC   300

GATTCTGGTG TCATTTCATC CAGGATCAGT TAATGGAGAG CACTTTTCTA GTAGTCAAAA   360

CTGATGGAGA AGCACAACAA AAGGCCATTG ACCACGTGTA TGAGAAACTG AAAGTGCTAG   420

AAGATGGAAT GAAGACCTAT CTGGGAGAAG GCAATGCTAT TATCTCTGGT GTTGAAAACA   480
```

```
ACTTTGGAAT CCTTGACATT GTGTTTTGTG CTTTATATGG TGCCTACAAG GCTCATGAAG      540

AAGTTATTGG CCTCAAGTTC ATAGTGCCAG AAAAGTTTCC TGTGTTGTTT TCTTGGTTGA      600

TGGCTATTGC TGAGGTTGAA GCTGTGAAAA TTGCAACTCC TCCACATGAA AAACAGTGG       660

GAATTCTTCA GTTGTTCAGG CTGTCTGCAC TGAAATCTTC TTCTGCCACA GAATGATATA      720

TACTTCAACA CTTTAATAGA CTGTCCATCG TTTGCTTCTT CTGCGAGTCT TTAGTGTATG      780

TATCTTTCAA TAACAGGATG AGTAACACCT GAGTATGTAA AGCGTGATGA TATAGAGATA      840

TACCTCTATA TATCAAATAC TCTTCTATAA AAAAAAAAAA AAAAA                     885
```

(2) INFORMATION FOR SEQ ID NO:24:

(i) SEQUENCE CHARACTERISTICS:
        (A) LENGTH: 235 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SS1.PK0020.B10

(xi) SEQUENCE DESCRIPTION: SEQ ID NO:24:

```
Met Ala Glu Gln Asp Lys Val Ile Leu His Gly Met Trp Ala Ser Pro
 1               5                  10                  15

Tyr Ala Lys Arg Val Glu Leu Ala Leu Asn Phe Lys Gly Ile Pro Tyr
                20                  25                  30

Glu Tyr Val Glu Glu Asp Leu Arg Asn Lys Ser Asp Leu Leu Leu Lys
            35                  40                  45

Tyr Asn Pro Val His Lys Lys Val Pro Val Leu Val His Asn Gly Lys
        50                  55                  60

Ala Ile Ala Glu Ser Met Val Ile Leu Glu Tyr Ile Asp Glu Thr Trp
65                  70                  75                  80

Lys Asp Gly Pro Lys Leu Leu Pro Ser Asp Ser Tyr Lys Arg Ala Gln
                85                  90                  95

Ala Arg Phe Trp Cys His Phe Ile Gln Asp Gln Leu Met Glu Ser Thr
            100                 105                 110

Phe Leu Val Val Lys Thr Asp Gly Glu Ala Gln Gln Lys Ala Ile Asp
        115                 120                 125

His Val Tyr Glu Lys Leu Lys Val Leu Glu Asp Gly Met Lys Thr Tyr
    130                 135                 140

Leu Gly Glu Gly Asn Ala Ile Ile Ser Gly Val Glu Asn Asn Phe Gly
145                 150                 155                 160

Ile Leu Asp Ile Val Phe Cys Ala Leu Tyr Gly Ala Tyr Lys Ala His
                165                 170                 175

Glu Glu Val Ile Gly Leu Lys Phe Ile Val Pro Glu Lys Phe Pro Val
            180                 185                 190

Leu Phe Ser Trp Leu Met Ala Ile Ala Glu Val Glu Ala Val Lys Ile
        195                 200                 205

Ala Thr Pro Pro His Glu Lys Thr Val Gly Ile Leu Gln Leu Phe Arg
    210                 215                 220

Leu Ser Ala Leu Lys Ser Ser Ser Ala Thr Glu
225                 230                 235
```

(2) INFORMATION FOR SEQ ID NO:25:

(i) SEQUENCE CHARACTERISTICS:
       (A) LENGTH: 991 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (F) TISSUE TYPE: SOYBEAN (vii) IMMEDIATE SOURCE:
       (B) CLONE: SSM.PK0067.G5

(xi) SEQUENCE DESCRIPTION: SEQ ID NO:25:

```
CTCGTGCCGT TTCTATAAAG GCCAAACTCA CAAACCACAC CCTAACAAAT TCATCTTATT    60

TTGCAACACA ATTCAATTTT GAGCACTTAC CAACACCACT TCCAATGGCT TCATATCATG   120

AAGAAGAAGT GAGGCTATTG GGCAAGTGGG CCAGCCCATT TAGCAACAGA GTAGACCTTG   180

CTCTCAAGCT CAAGGGTGTT CCCTACAAAT ACTCCGAGGA AGATCTTGCT AACAAGAGTG   240

CTGATCTTCT CAAGTACAAC CCCGTTCACA AGAAGGTTCC GGTTTTGGTC CACAATGGGA   300

ACCCATTGCC CGAGTCACTC ATCATTGTTG AATACATAGA TGAGACGTGG AAAAATAACC   360

CACTATTGCC TCAAGACCCA TATGAAAGAG CCTTGGCTCG TTTTTGGTCT AAGACCTTAG   420

ATGACAAGAT CTTGCCAGCT ATATGGAATG CTTGCTGGAG TGACGAGAAT GGGCGTGAGA   480

AAGCAGTGGA GGAAGCCTTG GAAGCATTGA AAATCCTACA GGAAACACTG AAAGACAAGA   540

AATTCTTTGG AGGAGAGAGC ATAGGATTGG TAGATATTGC TGCCAATTTC ATTGGGTATT   600

GGGTTGCCAT ATTGCAAGAG ATTGCAGGGT TGGAGTTGCT CACCATTGAG AAATTTCCCA   660

AGTTATATAA TTGGAGTCAA GACTTTATCA ACCACCCTGT GATCAAGGAG GGTCTGCCTC   720

CTAGAGATGA ATTGTTTGCT TTCTTCAAAG CTTCTGCTAA AAAGTAGAAC CATTTTAGAG   780

GTAGGATTCA TAATAAGTTA GTATGATTTT GTTGGGAAAC AATTATCTTG TTGTGAGCAA   840

AGGATTGTTC TGTTTTAAAT TTAATTGACT GTGATTTGGT TGGGTATTGG CTATTTTAAT   900

TTTAACTAAA AAAGTGTTC AGTTTTAAAA AAAAAAAAA AAAAAAAAA AAAAAAAAA    960

AAAAAAAAAA AAAAAAAAAA AAAAAAAAA A                                991
```

(2) INFORMATION FOR SEQ ID NO:26:

(i) SEQUENCE CHARACTERISTICS:
       (A) LENGTH: 220 amino acids
       (B) TYPE: amino acid
       (C) STRANDEDNESS: Not Relevant
       (D) TOPOLOGY: Not Relevant (ii) MOLECULE TYPE: protein (vi) ORIGINAL SOURCE:
       (F) TISSUE TYPE: SOYBEAN (vii) IMMEDIATE SOURCE:
       (B) CLONE: SSM.PK0067.G5

(xi) SEQUENCE DESCRIPTION: SEQ ID NO:26:

```
Met Ala Ser Tyr His Glu Glu Glu Val Arg Leu Leu Gly Lys Trp Ala
1               5                   10                  15

Ser Pro Phe Ser Asn Arg Val Asp Leu Ala Leu Lys Leu Lys Gly Val
```

```
                  20                  25                  30
Pro Tyr Lys Tyr Ser Glu Glu Asp Leu Ala Asn Lys Ser Ala Asp Leu
         35                  40                  45

Leu Lys Tyr Asn Pro Val His Lys Lys Val Pro Val Leu Val His Asn
 50                  55                  60

Gly Asn Pro Leu Pro Glu Ser Leu Ile Ile Val Glu Tyr Ile Asp Glu
 65                  70                  75                  80

Thr Trp Lys Asn Asn Pro Leu Leu Pro Gln Asp Pro Tyr Glu Arg Ala
                 85                  90                  95

Leu Ala Arg Phe Trp Ser Lys Thr Leu Asp Asp Lys Ile Leu Pro Ala
             100                 105                 110

Ile Trp Asn Ala Cys Trp Ser Asp Glu Asn Gly Arg Glu Lys Ala Val
             115                 120                 125

Glu Glu Ala Leu Glu Ala Leu Lys Ile Leu Gln Glu Thr Leu Lys Asp
 130                 135                 140

Lys Lys Phe Phe Gly Gly Glu Ser Ile Gly Leu Val Asp Ile Ala Ala
145                 150                 155                 160

Asn Phe Ile Gly Tyr Trp Val Ala Ile Leu Gln Glu Ile Ala Gly Leu
             165                 170                 175

Glu Leu Leu Thr Ile Glu Lys Phe Pro Lys Leu Tyr Asn Trp Ser Gln
             180                 185                 190

Asp Phe Ile Asn His Pro Val Ile Lys Glu Gly Leu Pro Pro Arg Asp
             195                 200                 205

Glu Leu Phe Ala Phe Phe Lys Ala Ser Ala Lys Lys
             210                 215                 220

(2) INFORMATION FOR SEQ ID NO:27:

(i) SEQUENCE CHARACTERISTICS:
        (A) LENGTH: 1024 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (F) TISSUE TYPE: SOYBEAN (vii) IMMEDIATE SOURCE:
        (B) CLONE: SE1.PK0017.F5

(xi) SEQUENCE DESCRIPTION: SEQ ID NO:27:

CCAAATCTTA AAAATATTCA GTGAAGATCA ACCTCAATGG CATCTCTTGG CGTGCGACCA      60

GTTCTTCCCC CTCCATTAAC TTCCATCTCC GACCCACCTC CTCTTTTCGA TGGCACCACC    120

AGGTTGTACA TCAGTTATTC TTGCCCCTAT GCACAACGTG TGTGGATCGC TAGGAACTAC    180

AAGGGGCTAC AAGATAAGAT CAATTTGGTC CCTATTAACC TTCAAGACAG GCCAGCTTGG    240

TATAAGGAGA AGTCTACCC TGAAAATAAG GTGCCATCCT GGAGCACAA TGGCAAGGTG      300

TTGGGAGAAA GTCTTGATTT GATCAAATAT GTAGATGCAA ACTTTGAAGG ACACCTTTG     360

TTTCCCAGTG ATCCTGCCAA GAAAGAGTTC GGTGAGCAAT TGATATCCCA TGTTGATACA    420

TTCAGCAAAG ACCTGTTCGT TTCATTGAAA GGGGATGCTG TACAGCAAGC CAGTCCCGCT    480

TTTGAATACT GGAGAATGC TCTTGGTAAA TTTGATGATG GGCCATTCTT GCTTGGCCAA     540

TTCAGTTTGG TGGATATTGC TTATATTCCA TTTGTTGAAA GATTCCAAAT TGTCTTTGCT    600

GAGGTGTTCA ACATGACAT CACAGAAGGA AGGCCTAAAC TTGCAACATG GTTTGAGGAG     660
```

```
TTGAATAAGC TAAATGCTTA TACCGAGACT AGAGTCGATC CTCAGGAGAT CGTTGATCTT    720

TTCAAGAAAC GCTTCCTGCC TCAACAGTGA ACGTTGTATT GCTGCAGGCT TCCTCTAAAA    780

TGTAGACTCT GCCCATATAG CGTCCTTTCA TTCACGGGAT GGGATGCATC TGCAGTCAAA    840

TGTCGGTTGT GTTTATCTGC CAGAGTTGCA GGATAGTTTG AAGTCATAAT CACGTTCATT    900

TTTCAGCTTG TTTGTTTGAT GTCATAATAA TGTTTATGTA CCAGTTTGTG ATCACTGATC    960

AATATGATAT AATGACCAAT ATGGTATTAT TATCCTATTT GAACTAAAAA AAAAAAAAA    1020

AAAA                                                                1024
```

(2) INFORMATION FOR SEQ ID NO:28:

(i) SEQUENCE CHARACTERISTICS:
        (A) LENGTH: 237 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: SOYBEAN (vii) IMMEDIATE SOURCE:
        (B) CLONE: SE1.PK0017.F5

(xi) SEQUENCE DESCRIPTION: SEQ ID NO:28:

```
Met Ala Ser Leu Gly Val Arg Pro Val Leu Pro Pro Leu Thr Ser
1               5                   10                  15

Ile Ser Asp Pro Pro Leu Phe Asp Gly Thr Thr Arg Leu Tyr Ile
                20                  25                  30

Ser Tyr Ser Cys Pro Tyr Ala Gln Arg Val Trp Ile Ala Arg Asn Tyr
            35                  40                  45

Lys Gly Leu Gln Asp Lys Ile Asn Leu Val Pro Ile Asn Leu Gln Asp
    50                  55                  60

Arg Pro Ala Trp Tyr Lys Glu Lys Val Tyr Pro Glu Asn Lys Val Pro
65                  70                  75                  80

Ser Leu Glu His Asn Gly Lys Val Leu Gly Glu Ser Leu Asp Leu Ile
                85                  90                  95

Lys Tyr Val Asp Ala Asn Phe Glu Gly Thr Pro Leu Phe Pro Ser Asp
                100                 105                 110

Pro Ala Lys Lys Glu Phe Gly Glu Gln Leu Ile Ser His Val Asp Thr
            115                 120                 125

Phe Ser Lys Asp Leu Phe Val Ser Leu Lys Gly Asp Ala Val Gln Gln
    130                 135                 140

Ala Ser Pro Ala Phe Glu Tyr Leu Glu Asn Ala Leu Gly Lys Phe Asp
145                 150                 155                 160

Asp Gly Pro Phe Leu Leu Gly Gln Phe Ser Leu Val Asp Ile Ala Tyr
                165                 170                 175

Ile Pro Phe Val Glu Arg Phe Gln Ile Val Phe Ala Glu Val Phe Lys
                180                 185                 190

His Asp Ile Thr Glu Gly Arg Pro Lys Leu Ala Thr Trp Phe Glu Glu
            195                 200                 205

Leu Asn Lys Leu Asn Ala Tyr Thr Glu Thr Arg Val Asp Pro Gln Glu
    210                 215                 220

Ile Val Asp Leu Phe Lys Lys Arg Phe Leu Pro Gln Gln
225                 230                 235
```

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:29:

GAYGARGANC TNCTNGAYTT YTGG                                          24

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:30:

GACTCGAGTC GACATGCTT                                                19

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:31:

CATATGAGTG ATGAGGTAGT GTTATTAGAT TTCTGG                             36

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:32:

TTATTACACA AATATTACTT ATTTGAAAGG CTAA                               34

SOYBEAN GLUTATHIONE-S-TRANSFERASE ENZYMES

This is a division of application Ser. No. 08/924,747 filed Sep. 5, 1997, now U.S. Pat. No. 6,063,570.

FIELD OF THE INVENTION

This invention is in the field of plant molecular biology. More specifically, this invention pertains to nucleic acid fragments encoding soybean glutathione-S-transferase (GST) enzymes involved in the detoxification of xenobiotic compounds in plants and seeds.

BACKGROUND OF THE INVENTION

Glutathione-S-transferases (GST) are a family of enzymes which catalyze the conjugation of glutathione, homoglutathione (hGSH) and other glutathione-like analogs via a sulfhydryl group, to a large range of hydrophobic, electrophilic compounds. The conjugation can result in detoxification of these compounds. GST enzymes have been identified in a range of plants including maize (Wosnick et al., *Gene* (Amst) 76 (1) (1989) 153–160; Rossini et al., *Plant Physiology* (Rockville) 112 (4) (1996) 1595–1600; Holt et al., *Planta* (Heidelberg) 196 (2) (1995) 295–302), wheat (Edwards et al., *Pestic. Biochem. Physiol.* (1996) 54(2), 96–104), sorghum (Hatzios et al., *J. Environ. Sci. Health,* Part B (1996), B31(3), 545–553), arabidopsis (Van Der Kop et al., *Plant Molecular Biology* 30 (4) (1996), sugarcane (Singhal et al., *Phytochemistry* (OXF) 30 (5) (1991) 1409–1414), soybean (Flury et al., *Physiologia Plantarum* 94 (1995) 594–604) and peas (Edwards R., *Physiologia Plantarum* 98 (3) (1996) 594–604). GST's can comprise a significant portion of total plant protein, for example attaining from 1 to 2% of the total soluble protein in etiolated maize seedlings (Timmermann, *Physiol. Plant.* (1989) 77(3), 465–71).

Glutathione S-transferases (GSTs; EC 2.5.1.18) catalyze the nucleophilic attack of the thiol group of GSH to various electrophilic substrates. Their functions and regulation in plants has been recently reviewed (Marrs et al., *Annu Rev Plant Physiol Plant Mol Biol* 47:127–58 (1996); Droog, F. *J Plant Growth Regul* 16:95–107, (1997)). They are present at every stage of plant development from early embryogenesis to senescence and in every tissue type examined. The agents that have been shown to cause an increase in GST levels have the potential to cause oxidative destruction in plants, suggesting a role for GSTs in the protection from oxidative damage. In addition to their role in the protection from oxidative damage, GSTs have the ability to nonenzymatically bind certain small molecules, such as auxin (Zettl, et al., *PNAS* 91: 689–693, (1994)) and perhaps regulate their bioavailability. Furthermore the addition of GSH to a molecule serves as an "address" to send that molecule to the plant vacuole (Marrs, et al., *Nature* 375: 397–400, (1995)).

GSTs have also been implicated in the detoxification of certain herbicides. Maize GSTs have been well characterized in relation to herbicide metabolism. Three genes from maize have been cloned: GST 29 (Shah et al., *Plant Mol Biol* 6, 203–211(1986)), GST 27 (Jepson et al., *Plant Mol Biol* 26:1855–1866, (1994)), GST 26 (Moore et al., *Nucleic Acids Res* 14:7227–7235 (1986)). These gene products form four GST isoforms: GST I (a homodimer of GST 29), GST II (a heterodimer of GST 29 and GST 27), GST III (a homodimer of GST 26), and GST IV (a homodimer of GST 27). GST 27 is highly inducible by safener compounds (Jepson (1994) supra; Holt et al., *Planta* 196:295–302, (1995)) and overexpression of GST 27 in tobacco confers alachlor resistance to transgenic tobacco (Jepson, personal communication). Additionally Bridges et al. (U.S. Pat. No. 5,589,614) disclose the sequence of a maize derived GST isoform II promoter useful for the expression of foreign genes in maize and wheat. In soybean, herbicide compounds conjugated to hGSH have been detected and correlated with herbicide selectivity (Frear et al., *Physiol* 20: 299–310 (1983); Brown et al., *Pest Biochem Physiol* 29:112–120, (1987)). This implies that hGSH conjugation is an important determinant in soybean herbicide selectivity although this hypothesis has not been characterized on a molecular level.

Glutathione (the tripeptide γ-glu-cys-gly, or GSH) is present in most plants and animals. However, in some plants from the family Leguminaceae the major free thiol is homoglutathione. For example, soybeans (*Glycine max*) have nearly undetectable levels of glutathione with the tripeptide homoglutathione (γ-glu-cys-β-ala) apparently substituting for the same functions. Some herbicides are detoxified in soybeans by homoglutathione conjugation catalyzed by glutathione S-transferase (GST) enzyme(s).

Homoglutathione (hGSH) was originally detected in *Phaseolus vulgaris* and several other leguminous species (Price, C. A., *Nature* 180: 148–149, (1957)). The structure of hGSH (Carnegie, P. R., *Biochemical Journal* 89:471–478 (1963)) was determined to be the tripeptide γ-glu-cys-β-ala. Homoglutathione has not been found in non-leguminous species. In plants from the family Leguminaceae, the ratio of hGSH to GSH varies according to both species and tissue examined. In seeds and leaves of the tribe Vicieae, only traces of hGSH were found in addition to the main thiol GSH, whereas in roots the hGSH content exceeded the GSH content. The tribe Trifolieae contained both tripeptides and in the tribe Phaseoleae, hGSH predominated. In soybean (*Glycine max*), a member of the Phaseoleae, hGSH constitutes 99% of the free thiol in leaves and seeds and greater than 95% of the free thiol in soybean roots (Klapheck, S., *Physiolgia Plantarum* 74: 727–732 (1988)). As such, it is essential that soybean glutathione S-transferases be able to efficiently utilize hGSH.

Some efforts have been made to alter plant phenotypes by the expression of either plant or mammalian foreign GST genes or their promoters in mature plant tissue. For example, Helmer et al. (U.S. Pat. No. 5,073,677) teach the expression of a rat GST gene in tobacco under the control of a strong plant promoter. Similarly, Jepson et al. (WO 97/11189) disclose a chemically inducible maize GST promoter useful for the expression of foreign proteins in plants; Chilton et al. (EP 256223) discuss the construction of herbicide tolerant plants expressing a foreign plant GST gene; and Bieseler et al. (WO 96/23072) teach DNA encoding GSTIIIc, its recombinant production and transgenic plants containing the DNA having a herbicide-tolerant phenotype.

Manipulation of nucleic acid fragments encoding soybean GST to use in screening in assays, the creation of herbicide-tolerant transgenic plants, and altered production of GST enzymes depend on the heretofore unrealized isolation of nucleic acid fragments that encode all or a substantial portion of a soybean GST enzyme.

SUMMARY OF THE INVENTION

The present invention provides nucleic acid fragments isolated from soybean encoding all or a substantial portion of a GST enzyme. The isolated nucleic acid fragment is selected from the group consisting of (a) an isolated nucleic acid fragment encoding all or a substantial portion of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28; (b) an isolated nucleic acid fragment that is substantially similar to an isolated nucleic acid fragment encoding all or a substantial portion of the amino acid sequence sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28; and (c) an isolated nucleic acid fragment that is complementary to (a) or (b). The nucleic acid fragments and corresponding polypeptides are contained in the accompanying Sequence Listing and described in the Brief Description of the Invention.

In another embodiment, the instant invention relates to chimeric genes encoding soybean GST enzymes or to chimeric genes that comprise nucleic acid fragments as described above, the chimeric genes operably linked to suitable regulatory sequences, wherein expression of the chimeric genes results in altered levels of the encoded enzymes in transformed host cells.

The present invention further provides a transformed host cell comprising the above described chimeric gene. The transformed host cells can be of eukaryotic or prokaryotic origin. The invention also includes transformed plants that arise from transformed host cells of higher plants, and from seeds derived from such transformed plants, and subsequent progeny.

Additionally, the invention provides methods of altering the level of expression of a soybean GST enzyme in a host cell comprising the steps of; (i) transforming a host cell with the above described chimeric gene and; (ii) growing the transformed host cell produced in step (i) under conditions that are suitable for expression of the chimeric gene wherein expression of the chimeric gene results in production of altered levels of a plant GST enzyme in the transformed host cell relative to expression levels of an untransformed host cell.

In an alternate embodiment, the present invention provides methods of obtaining a nucleic acid fragment encoding all or substantially all of the amino acid sequence encoding a soybean GST enzyme comprising either hybridization or primer-directed amplification methods known in the art and using the above described nucleic acid fragment. A primer-amplification-based method uses SEQ ID NOS.: 1, 3, 5, 7, 9, 11, 13, 15, 17, 19, 21, 23, 25, or 27. The product of these methods is also part of the invention.

Another embodiment of the invention includes a method for identifying a compound that inhibits the activity of a soybean GST enzyme encoded by the nucleic acid fragment and substantially similar and complementary nucleic acid fragments of SEQ ID NOS.: 1–28. The method has the steps: (a) transforming a host cell with the above described chimeric gene; (b) growing the transformed host cell under conditions that are suitable for expression of the chimeric gene wherein expression of the chimeric gene results in production of the GST enzyme; (c) optionally purifying the GST enzyme expressed by the transformed host cell; (d) contacting the GST enzyme with a chemical compound of interest; and (e) identifying the chemical compound of interest that reduces the activity of the soybean GST enzyme relative to the activity of the soybean GST enzyme in the absence of the chemical compound of interest.

This method may further include conducting step (d) in the presence of at least one electrophilic substrate and at least one thiol donor. The isolated nucleic acid fragments of this method are chosen from the group represented by SEQ ID NOS.: 1, 3, 5, 7, 9, 11, 13, 15, 17, 19, 21, 23, 25 and 27, and the soybean GST enzyme is selected from the group consisting of SEQ ID NOS.: 2, 4, 6, 8, 10, 12, 14, 16, 18, 20, 22, 24, 26 and 28.

The invention further provides a method for identifying a chemical compound that inhibits the activity of the soybean GST enzyme as described herein, wherein the identification is based on a comparison of the phenotype of a plant transformed with the above described chimeric gene contacted with the inhibitor candidate with the phenotype of a transformed plant that is not contacted with the inhibitor candidate. The isolated nucleic acid fragment of this method is selected from the group consisting of SEQ ID NOS.: 1, 3, 5, 7, 9, 11, 13, 15, 17, 19, 21, 23, 25, 25, and 27 and the soybean GST enzyme is selected from the group consisting of SEQ ID NOS.: 2, 4, 6, 8, 10, 12, 14, 16, 18, 20, 22, 24, 26, and 28.

In another embodiment, the invention provides a method for identifying a substrate for the soybean GST enzyme. The method comprises the steps of: (a) transforming a host cell with a chimeric gene comprising the nucleic acid fragment as described herein, the chimeric gene encoding a soybean GST enzyme operably linked to at least one suitable regulatory sequence; (b) growing the transformed host cell of step (a) under conditions that are suitable for expression of the chimeric gene resulting in production of the GST enzyme; (c) optionally purifying the GST enzyme expressed by the transformed host cell; (d) contacting the GST enzyme with a substrate candidate; and (e) comparing the activity of soybean GST enzyme with the activity of soybean GST enzyme that has been contacted with the substrate candidate and selecting substrate candidates that increase the activity of the sobyean GST enzyme relative to the activity of soybean GST enzyme in the absence of the substrate candidate. More preferably, step (d) of this method is carried out in the presence of at least one thiol donor. The isolated nucleic acid fragment of this method is selected from the group consisting of SEQ ID NOS.: 1, 3, 5, 7, 9, 11, 13, 15, 17, 19, 21, 23, 25, and 27 and the soybean GST enzyme is selected from the group consisting of SEQ ID NOS.: 2, 4, 6, 8, 10, 12, 14, 16, 18, 20, 22, 24, 26, and 28.

Alternatively, methods are provided for identifying a soybean GST substrate candidate wherein the identification of the substrate candidate is based on a comparison of the phenotype of a host cell transformed with a chimeric gene expressing a soybean GST enzyme and contacted with a substrate candidate with the phenotype of a similarly transformed host cell grown without contact with a substrate candidate.

The isolated nucleic acid fragment of this method is selected from the group consisting of SEQ ID NOS.: 1, 3, 5, 7, 9, 11, 13, 15, 17, 19, 21, 23, 25, and 27 and the soybean GST enzyme is selected from the group consisting of SEQ ID NOS.: 2, 4, 6, 8, 10, 12, 14, 16, 18, 20, 22, 24, 26, and 28.

BRIEF DESCRIPTION OF SEQUENCE DESCRIPTIONS AND BIOLOGICAL DEPOSITS

The invention can be more fully understood from the following detailed description and the accompanying sequence descriptions and biological deposits which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence comprising the cDNA insert in clone se1.27b04 encoding a soybean type I GST.

SEQ ID NO:2 is the deduced amino acid sequence of the nucleotide sequence comprising the cDNA insert in clone se1.27b04.

SEQ ID NO:3 is the nucleotide sequence comprising the cDNA insert in clone ssm.pk0026.g11 encoding a soybean type II GST.

SEQ ID NO:4 is the deduced amino acid sequence of the nucleotide sequence comprising the cDNA insert in clone ssm.pk0026.g11.

SEQ ID NO:5 is the nucleotide sequence comprising the cDNA insert in clone GSTa encoding a soybean type III GST.

SEQ ID NO:6 is the deduced amino acid sequence of the nucleotide sequence comprising the cDNA insert in clone GSTa.

SEQ ID NO:7 is the nucleotide sequence comprising the cDNA insert in clone se3.03b09 encoding a soybean type III GST.

SEQ ID NO:8 is the deduced amino acid sequence of the nucleotide sequence comprising the cDNA insert in clone se3.03b09.

SEQ ID NO:9 is the nucleotide sequence comprising the cDNA insert in clone se6.pk0037.h4 encoding a soybean type III GST.

SEQ ID NO:10 is the deduced amino acid sequence of the nucleotide sequence comprising the cDNA insert in clone se6.pk0037.h4.

SEQ ID NO:11 is the nucleotide sequence comprising the cDNA insert in clone se6.pk0048.d7 encoding a soybean type III GST.

SEQ ID NO:12 is the deduced amino acid sequence of the nucleotide sequence comprising the cDNA insert in clone se6.pk0048.d7.

SEQ ID NO:13 is the nucleotide sequence comprising the cDNA insert in clone ses8w.pk0028.c6 encoding a soybean type III GST.

SEQ ID NO:14 is the deduced amino acid sequence of the nucleotide sequence comprising the cDNA insert in clone ses8w.pk0028.c6.

SEQ ID NO:15 is the nucleotide sequence comprising the cDNA insert in clone sr1.pk0011.d6 encoding a soybean type III GST.

SEQ ID NO:16 is the deduced amino acid sequence of the nucleotide sequence comprising the cDNA insert in clone sr1.pk0011.d6.

SEQ ID NO:17 is the nucleotide sequence comprising the cDNA insert in clone ss1.pk0002.f7 encoding a soybean type III GST.

SEQ ID NO:18 is the deduced amino acid sequence of the nucleotide sequence comprising the cDNA insert in clone ss1.pk0002.f7.

SEQ ID NO:19 is the nucleotide sequence comprising the cDNA insert in clone ss1.pk0005.e6 encoding a soybean type III GST.

SEQ ID NO:20 is the deduced amino acid sequence of the nucleotide sequence comprising the cDNA insert in clone ss1.pk0005.e6.

SEQ ID NO:21 is the nucleotide sequence comprising the cDNA insert in clone ss1.pk0014.a1 encoding a soybean type III GST.

SEQ ID NO:22 is the deduced amino acid sequence of the nucleotide sequence comprising the cDNA insert in clone ss1.pk0014.a1.

SEQ ID NO:23 is the nucleotide sequence comprising the cDNA insert in clone ss1.pk0020.b10 encoding a soybean type III GST.

SEQ ID NO:24 is the deduced amino acid sequence of the nucleotide sequence comprising the cDNA insert in clone ss1.pk0020.b10.

SEQ ID NO:25 is the nucleotide sequence comprising the cDNA insert in clone ssm.pk0067.g5 encoding a soybean type III GST.

SEQ ID NO:26 is the deduced amino acid sequence of the nucleotide sequence comprising the cDNA insert in clone ssm.pk0067.g5.

SEQ ID NO:27 is the nucleotide sequence comprising the cDNA insert in clone se1.pk0017.f5 encoding a soybean type IV GST.

SEQ ID NO:28 is the deduced amino acid sequence of the nucleotide sequence comprising the cDNA insert in clone se1.pk0017.f5.

The transformed *E. coli* sr1.pk0011.d6/pET30(LIC)BL21 (DE3) comprising the *E. coli* host BL21(DE3), containing the gene sr1.pk0011.d6 in a pET30(LIC) vector encoding a soybean type III GST was deposited on Aug. 21, 1997 with the American Type Culture Collection (ATCC), 12301 Parklawn Drive, Rockville, Md. 20852 U.S.A. under the terms of the Budapest Treaty on the International Recognition of the Deposit of Micro-organisms for the Purpose of patent Procedure. The deposit is designated as ATCC 98512.

DETAILED DESCRIPTION OF THE INVENTION

The present invention provides novel GST nucleotide sequences and encoded proteins isolated from soybean. GST enzymes are known to function in the process of detoxification of a variety of xenobiotic compounds in plants, most notably, herbicides. Nucleic acid fragments encoding at least a portion of several soybean GST enzymes have been isolated and identified by comparison of random plant cDNA sequences to public databases containing nucleotide and protein sequences using the BLAST algorithms well known to those skilled in the art. The sequences of the present invention are useful in the construction of herbicide-tolerant transgenic plants, in the recombinant production of GST enzymes, in the development of screening assays to identify compounds inhibitory to the GST enzymes, and in screening assays to identify chemical substrates of the GSTs.

In the context of this disclosure, a number of terms shall be utilized.

"Glutathione S-Transferase" or "GST" refers to any plant-derived glutathione S-transferase (GST) enzyme capable of catalyzing the conjugation of glutathione, homoglutathione and other glutathione-like analogs via a sulfhydryl group to hydrophobic and electrophilic compounds. The term "GST" includes amino acid sequences longer or shorter than the length of natural GSTs, such as functional hybrid or partial fragments of GSTs, or their analogues. "GST" is not intended to be limited in scope on the basis of enzyme activity and may encompass amino acid sequences that possess no measurable enzyme activity but are substantially similar to those sequences known in the art to possess the above-mentioned glutathione conjugating activity.

The term "class" or "GST class" refers to a grouping of the various GST enzymes according to amino acid identity. Currently, four classes have been identified and are referred to as "GST class I" "GST class II", "GST class III" and "GST class IV". The grouping of plant GSTs into three classes is described by Droog et al. (*Plant Physiology* 107:1139–1146 (1995)). All available amino acid sequences were aligned using the Wisconsin Genetics Computer Group package (Wisconsin Package Version 9.0, Genetics Computer Group (GCG), Madison, Wis.), and graphically represented on a phylogenetic tree. Three groups were identified: class one including the archetypical sequences from maize GST I (X06755) and GST III (X04375); class two including the archetypical sequence from *Dianthus caryophyllus* (M64628); and class three including the archetypical sequence soybean GH2/4 (M20363). Recently, Applicants have established a further subgroup of the plant GSTs known as class IV GSTs with its archetypical sequence being In2-1 (X58573).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1X SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the GST enzymes as set forth in SEQ ID Nos: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28. The skilled artisan is well aware of the "codon-bias" exhibited by a specific host cell in usage of nucleotide codons to specify a given amino acid. Therefore, when synthesizing a gene fox improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. ((1989) *Plant Cell* 1:671–680).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.*100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

The term "herbicide-tolerant plant" as used herein is defined as a plant that survives and preferably grows normally at a usually effective dose of a herbicide. Herbicide tolerance in plants according to the present invention refers to detoxification mechanisms in a plant, although the herbicide binding or target site is still sensitive.

"Thiol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheramones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other GST enzymes, either as cDNAs or genomic DNAs, could be isolated directly by using all or a portion of the instant nucleic acid fragments as DNA hybridization probes to screen libraries from any desired plant using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol* 36:1; Maniatis).

The nucleic acid fragments of the instant invention may be used to create transgenic plants in which the disclosed GST enzymes are present at higher or lower levels than normal or in cell types or developmental stages in which they are not normally found. This would have the effect of altering the level of GST enzyme available as well as the herbicide-tolerant phenotype of the plant.

Overexpression of the GST enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a GST coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence for GST, should be capable of promoting expression of the GST such that the transformed plant is tolerant to an herbicide due to the presence of, or increased levels of, GST enzymatic activity. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed Appl.*, 618 (1–2) (1993) 133–145), Western analysis of protein expression, or phenotypic analysis.

For some applications it will be useful to direct the instant GST enzymes to different cellular compartments or to facilitate enzyme secretion from a recombinant host cell. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.*100:1627–1632 (1992)) added and/or with targeting sequences that are already present removed. While the references cited give examples of each of these, the list is not exhaustive and more targeting signals of utility may be discovered in the future that are useful in the invention.

It may also be desirable to reduce or eliminate expression of the genes encoding the instant GST enzymes in plants. In order to accomplish this, chimeric genes designed for co-suppression of the instant GST enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

Plants transformed with the present GST genes will have a variety of phenotypes corresponding to the various properties conveyed by the GST class of proteins. Glutathione conjugation catalyzed by GSTs are known to result in sequestration and detoxification of a number of herbicides and other xenobiotics (Marrs et al., *Annu. Rev. Plant Physiol. Plant Mol. Biol.* 47:127–58 (1996)) and thus will be expected to produce transgenic plants with this phenotype. Other GST proteins are known to be induced by various environmental stresses such as salt stress (Roxas, et al., *Stress tolerance in transgenic seedlings that overexpress glutathione S-transferase,* Annual Meeting of the American Society of Plant Physiologists, (August 1997), abstract 1574, Final Program, Plant Biology and Supplement to Plant Physiology, 301), exposure to ozone (Sharma et al., *Plant Physiology,* 105 (4) (1994) 1089–1096), and exposure to industrial pollutants such as sulfur dioxide (Navari-Izzo et al., *Plant Science* 96 (1–2) (1994) 31–40). It is contemplated that transgenic plants, tolerant to a wide variety of stresses, may be produced by the present method by expressing foreign GST genes in suitable plant hosts.

The instant GST enzymes produced in heterologous host cells, particularly in the cells of microbial hosts, can be used to prepare antibodies to the enzymes by methods well known to those skilled in the art. The antibodies are useful for detecting the enzymes in situ in cells or in vitro in cell extracts. Preferred heterologous host cells for production of the instant GST enzymes are microbial hosts. Microbial expression systems and expression vectors containing regulatory sequences that direct high level expression of foreign proteins are well known to those skilled in the art. Any of these could be used to construct chimeric genes for production of the instant GST enzymes. These chimeric genes could then be introduced into appropriate microorganisms via transformation to provide high level expression of the enzymes.

Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the GST enzymes in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary, however, it is most preferred if included.

An example of a vector for high level expression of the instant GST enzymes in a bacterial host is provided (Example 5).

Additionally, the instant soybean GST enzymes can be used as a targets to facilitate design and/or identification of inhibitors of the enzymes that may be useful as herbicides or herbicide synergists. This is desirable because the enzymes described herein catalyze the sulfhydryl conjugation of glutathione to compounds toxic to the plant. Conjugation can result in detoxification of these compounds. It is likely that inhibition of the detoxification process will result in inhibition of plant growth or plant death. Thus, the instant soybean GST enzymes could be appropriate for new herbicide or herbicide synergist discovery and design.

All or a portion of the nucleic acid fragments of the instant invention may also be used as probes for genetically and physically mapping the genes that they are a part of, and as markers for traits linked to expression of the instant enzymes. Such information may be useful in plant breeding in order to develop lines with desired phenotypes or in the identification of mutants.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., (1980) *Am. J. Hum. Genet.* 32:314–331).

The production and use of plant gene-derived probes for use in genetic mapping are described by Bematzky, R. and Tanksley, S. D. (*Plant Mol. Biol. Reporter* 4(1):37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., In: *Nonmammalian Genomic Analysis: A Practical Guide,* Academic press, pp. 319–346 (1996), and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, this is generally not necessary for mapping methods. Such information may be useful in plant breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain he essential characteristics of this invention, and without departing from the spirit and scope thereof, can make various changes and modifications of the invention to adapt it to various usages and conditions.

GENERAL METHODS

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1

Composition of cDNA Libraries; Isolation and Sequencing of cDNA Clones cDNA libraries representing mRNAs from various soybean tissues were prepared. The characteristics of the libraries are described in Table 1.

TABLE 1 cDNA Libraries From Soybean Tissues

| Library | GST Class | Clone | Tissue |
| --- | --- | --- | --- |
| se1 | I | se1.27b04 | Soybean embryo, |
| ssm | II | ssm.pk0026.g11 | soybean shoot meristem |
| NA | III | GSTa | NA |
| se3 | III | se3.03b09 | Soybean embryo, |
| se6 | III | se6.pk0037.h4 | Soybean embryo, |
| se6 | III | se6.pk0048.d7 | Soybean embryo, |
| ses8w | III | ses8w.pk0028.c6 | mature embryo 8 weeks after subculture |
| sr1 | III | sr1.pk0011.d6 | Soybean root library. |
| ss1 | III | ss1.pk0002.f7 | soybean seedling 5–10 day |
| ss1 | III | ss1.pk0005.e6 | soybean seedling 5–10 day |
| ss1 | III | ss1.pk0014.a1 | soybean seedling 5–10 day |
| ss1 | III | ss1.pk0020.b10 | soybean seedling 5–10 day |
| ssm | III | ssm.pk0067.g5 | soybean shoot meristem |
| se1 | IV | se1.pk0017.f5 | Soybean embryo, | cDNA Library Preparation

For clones other than GSTa, cDNA libraries were prepared in Uni-ZAP™ XR vectors according to the manufacturer's protocol (Stratagene Cloning Systems, La Jolla, Calif.). The Uni-ZAP™ XR libraries were converted into plasmid libraries according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., Science 252:1651 (1991)). The resulting ESTs were analyzed using a Perkin Elmer Model 377 fluorescent sequencer.

Cloning of GSTa

The GSTa clone was isolated and cloned using primers derived from a published GST sequence, GH2/4 (Flurry et al., *Physiologia Plantarum* 94 (1995) 594–604) according to the following protocol.

Soybeans (cv Williams 82) were germinated in vermiculite in a controlled growth room at 23° C. with 14-h light/10-h dark cycle at 330 $\mu E$ $m^{-2}s^{-1}$. One week old seedlings were treated with 1 mM 2,4-D for 24 h before harvest. Seedlings were frozen in liquid nitrogen and ground with a mortar and pestle and RNA was prepared using TriZol reagent (Life Technologies Bethesda, Md.). Approximately 1.5 $\mu g$ of total RNA was reverse transcribed using the GeneAmp Kit (Perkin Elmer, Branchburg, N.J.) and oligo dT primer. The resulting first strand cDNA was used as a template for PCR amplification with AmpliTaq (Perlin Elmer) and the following primers: primer 1: (GAY GAR GAN CTN CTN GAY TTY TGG) (SEQ ID NO:29) and primer 2: (GAC TCG AGT CGA CAT GCT $T_{16}$) (SEQ ID NO:30). Primer 1 and primer 3 (see below) were designed based on N-terminal protein sequence previously described (Flury et al., 1995, supra). A Perkin-Elmer Thermal Cycle was allowed to cycle at 95° C. for 30 sec, 52° C. for 30 sec and 72° C. for 30 sec for 30 cycles. The resulting PCR product was cloned in pCR2.1 (Invitrogen, San Diego, Calif.) according to the manufacturer's instructions, named pBD16 and sequenced using an ABI sequencer. Primer 1 was designed to take advantage of the lack of degeneracy for encoding tryptophan. Because of this, the clone did not include the entire coding region and a second round of PCR was performed using the following primers: Primer 3: CAT ATG AGT GAT GAG GTA GTG TTA TTA GAT TTC TGG (SEQ ID NO:31) and Primer 4: TTA TTA CAC AAA TAT TAC TTA TTT GAA AGG CTA A (SEQ ID NO:32) and using 0.002 $\mu g$ of linearized pBD16 as a template. Again, the resulting PCR product was cloned into pCR2.1 and named pBD17 and sequenced using an ABI sequencer. Additional gene specific primers were made and used to determine the complete sequence. All regions were sequenced at least two times in both directions. The nucleotide sequence and encoded protein sequence are shown in SEQ ID NO:5 and SEQ ID NO:6, respectively.

Example 2

Identification and Characterization of cDNA Clones cDNAs encoding soybean GST enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

All comparisons were done using the BLASTNnr algorithm. The results of the BLAST comparison is given in Table 2 and summarizes the clones and the sequences to which they have the most similarity. Each cDNA identified encodes at least a portion of either a GST Class I, II, III, or IV.

Example 5 describes the strategy for sequencing the above described clones.

TABLE 2

BLAST Results For Clones

| Clone | GST Class | Similarity Identified | SEQ ID NO. Base | Peptide | Blast Algorithm | pLog Score |
|---|---|---|---|---|---|---|
| se1.27b04 | I | X06754\|ZMGST1 Maize mRNA for GSH gluthathione S-transferase I | 1 | 2 | Nnr | 41.35 |
| ssm.pk0026.g11 | II | \|X58390\|DCCARSR8 D.caryophyllus CARSR8 mRNA for glutathione s-transferase | 3 | 4 | Nnr | 85.02 |
| GSTa | III | Y10820\|GMGLUTTR G.max mRNA for glutathione transferase | 5 | 6 | Nnr | 257.95 |
| se3.03b09 | III | M20363\|SOYHSP Soybean heat-shock protein (Gmhsp26-A) gene | 7 | 8 | Nnr | 28.72 |
| se6.pk0037.h4 | III | M20363\|SOYHSP Soybean heat-shock protein (Gmhsp26-A) gene, complete cds | 9 | 10 | Nnr | 247.44 |
| se6.pk0048.d7 | III | Y10820\|GMGLUTTR G.max mRNA for glutathione transferase | 11 | 12 | Nnr | 0.0 |
| ses8w.pk0028.c6 | III | M20363\|SOYHSP Soybean heat-shock protein (Gmhsp26-A) gene, complete cds. | 13 | 14 | Nnr | 269.17 |
| sr1.pk0011.d6 | III | U20809\|VRU20809 Vigna radiata clone MII-4 auxin-induced protein mRNA, partial cds | 15 | 16 | Nnr | 229.82 |
| ss1.pk0002.f7 | III | X68819\|GMGLYO G.max mRNA for Glyoxalase I | 17 | 18 | Nnr | 206.01 |
| ss1.pk0005.e6 | III | Y10820\|GMGLUTTR G.max mRNA for glutathione transferase | 19 | 20 | Xnr | 296.05 |
| ss1.pk0014.a1 | III | M20363\|SOYHSP Soybean heat-shock protein (Gmhsp26-A) gene, complete cds | 21 | 22 | Nnr | 166.96 |
| ss1.pk0020.b10 | III | M20363\|SOYHSP Soybean heat-shock protein (Gmhsp26-A) gene, complete cds. | 23 | 24 | Nnr | 34.76 |
| ssm.pk0067.g5 | III | M20363\|SOYHSP Soybean heat-shock protein (Gmhsp26-A) gene, complete cds | 25 | 26 | Nnr | 104.00 |
| se1.pk0017.f5 | IV | \|X58573\|ZMIN21 Maize In2-1 mRNA | 27 | 28 | Nnr | 72.04 |

Example 3

Expression of Chimeric Genes Encoding Soybean GST Enzymes in Maize Cells (Monocotyledon)

A chimeric gene comprising a cDNA encoding a soybean GST enzyme in sense orientation can be constructed by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 uL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty with the ATCC and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp., 7113 Benhart Dr., Raleigh, N.C.). Vector and insert DNA can be ligated at 15° C. overnight, essentially as described (Maniatis). The ligated DNA may then be used to transform E. coli XL1-Blue (Epicurian Coli XL-1; Stratagene). Bacterial transformants can be screened by restriction enzyme digestion of plasmid DNA and limited nucleotide sequence analysis using the dideoxy chain termination method (DNA Sequencing Kit, U.S. Biochemical). The resulting plasmid construct would comprise a chimeric gene encoding, in the 5' to 3' direction, the maize 27 kD zein promoter, a cDNA fragment encoding a plant gst enzyme, and the 10 kD zein 3' region.

The chimeric gene so constructed can then be introduced into corn cells by the following procedure. Immature corn embryos can be dissected from developing caryopses derived from crosses of the inbred corn lines H99 and LH132 (Indiana Agric. Exp. Station, Ind., USA). The embryos are isolated 10 to 11 days after pollination when they are 1.0 to 1.5 mm long. The embryos are then placed with the axis-side facing down and in contact with agarose-solidified N6 medium (Chu et al., *Sci. Sin.* Peking 18:659–668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany), may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. *Nature* 313:810–812 (1985)) and the 3M region of the nopaline synthase gene from the T-DNA of the Ti plasmid of *Agrobacterium tumefaciens*. The particle bombardment method (Klein et al., *Nature* 327:70–73 (1987)) may be used to transfer genes to the callus culture cells. According to this method, gold particles (1 μm in diameter) are coated with DNA using the following technique. Ten ug of plasmid DNAs are added to 50 μL of a suspension of gold particles (60 mg per mL). Calcium chloride (50 uL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 uL of ethanol. An aliquot (5 μL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr., Medina, Ohio), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks, the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from the transgenic callus by first transferring clusters of tissue to N6 medium supplemented with 0.2 mg per liter of 2,4-D. After two weeks, the tissue can be transferred to regeneration medium (Fromm et al., *Bio/Technology* 8:833–839 (1990)).

Example 4

Expression of Chimeric Genes in Tobacco Cells
(Dicotyledon)

Cloning sites (XbaI or SmaI) can be incorporated into the oligonucleotides to provide proper orientation of the DNA fragment when inserted into the digested vector pBI121 (Clonetech Inc., 6500 Donlon Rd, Somis, Calif.) or other appropriate transformation vector. Amplification could be performed as described above and the amplified DNA would then be digested with restriction enzymes XbaI and SmaI and fractionated on a 0.7% low melting point agarose gel in 40 mM Tris-acetate, pH 8.5, 1 mM EDTA. The appropriate band can be excised from the gel, melted at 68° C. and combined with a 13 kb XbaI-SmaI fragment of the plasmid pBI121 and handled as in Example 3. The resulting plasmid construct would comprise a chimeric gene encoding, in the 5' to 3' direction, right border region, the nos promoter linked to the NPT II gene and a nos terminator region followed by a cauliflower mosaic virus 35S promoter linked to a cDNA fragment encoding a plant GST enzyme and the nos terminator 3' region flanked by the left border region. The resulting plasmid could be mobilized into the *Agrobacterium* strain LBA4404/pAL4404 (Hoekema et al. *Nature* 303:179–180, (1983) using tri-parental matings (Ruvkin and Ausubel, *Nature* 289:85–88, (1981)). The resulting *Agrobacterium strains* could be then cocultivated with protoplasts (van den Elzen et al. *Plant Mol. Biol*, 5:149–154 (1985)) or leaf disks (Horsch et al. *Science* 227:1229–1231, (1985)) of *Nicotiana tabacum* cv Wisconsin 38 and kanamycin-resistant transformants would be selected. Kanamycin-resistant transformed tobacco plants would be regenerated.

Example 5

Expression Of Chimeric Genes In Microbial Cells
And Purification Of Gene Product Example 5 illustrates the expression of isolated full length genes encoding class I, II, III or IV GST proteins in *E. coli*.

All clones listed in Table 2 were selected on the basis of homology to known GSTs using the BLAST algorithm as described in Example 2. Plasmid DNA was purified using QIAFilter cartridges (Qiagen. Inc., 9600 De Soto Ave, Chatsworth, Calif.) according to the manufacturer's instructions. Sequence was generated on an ABI Automatic sequencer using dye terminator technology (U.S. Pat. No. 5,366,860; EP 272007) using a combination of vector and insert-specific primers. Sequence editing was performed in either DNAStar (DNA, Star Inc.) or the Wisconsin GCG program (Wisconsin Package Version 9.0, Genetics Computer Group (GCG), Madison, Wis.). All sequences represent coverage at least two times in both directions.

cDNA from fill length clones listed in Table 2 encoding the instant soybean GST enzymes were mserted into the ligation independent cloning (LIC) pET30 vector (Novagen, Inc., 597 Science Dr, Madison, Wis.) under the control of the T7 promoter, according to the manufacturer's instructions (see Novagen publications "LIC Vector Kits", publication number TB163 and U.S. Pat. No. 4,952,496). The vector was then used to transform BL21(DE3) competent E. coli hosts. Primers with a specific 3' extension designed for ligation independent cloning were designed to amplify the GST gene (Maniatis). Amplification products were gel-purified and annealed into the LIC vector after treatment with T4 DNA polymerase (Novagen). Insert-containing vectors were then used to transform NovaBlue competent E. coli cells and transformants were screened for the presence of viable inserts. Clones in the correct orientation with respect to the T7 promoter were transformed into BL21 (DE3) competent cells (Novagen) and selected on LB agar plates containing 50 µg/mL kanamycin. Colonies arising from this transformation were grown overnight at 37° C. in Lauria Broth to OD 600=0.6 and induced with 1 mM IPTG and allowed to grow for an additional two hours. The culture was harvested, resuspended in binding buffer, lysed with a French press and cleared by centrifugation.

Expressed protein was purified using the HIS binding kit (Novagen) according to the manufacturer's instructions. Purified protein was examined on 15–20% SDS Phast Gels (Bio-Rad Laboratories, 861 Ridgeview Dr, Medina, Ohio) and quantitated spectrophotometrically using BSA as a standard. Protein data is tabulated below in Table 3.

TABLE 3

Protein Expression Data

| CLONE | OD.280 |
|---|---|
| se1.27b04 | 0.5 |
| ssm.pk0026.g11 | 0.44 |
| GSTa | 53.6 |
| se3.03b09 | 29.1 |
| se6.pk0037.h4 | 0.6 |
| se6.pk0048.d7 | 1.41 |
| ses8w.pk0028.c6 | 0.56 |
| sr1.pk0011.d6 | 0.55 |
| ss1.pk0002.f7 | 0.70 |
| ss1.pk0005.e6 | 0.51 |
| ss1.pk0014.a1 | 0.62 |

TABLE 3-continued

Protein Expression Data

| CLONE | OD.280 |
|---|---|
| ss1.pk0020.b10 | 1.14 |
| ssm.pk0067.g5 | 1.64 |
| se1.pk0017.f5 | 0.37 |

Example 6

Screening Of Expressed GST Enz mes For Substrate Metabolism

The GST enzymes, expressed and purified as described in Example 5 were screened for their ability to metabolize a variety of substrates. Substrates tested included the three herbicide electrophilic substrates chlorimuron ethyl, alachlor, and Atrazine, and four model electrophilic substrates, 1-chloro-2,4-dinitro-benzene (CDNB), ethacrynic acid, t-stilbene oxide, and 1,2-epoxy-3-(p-nitrophenoxy) propane. The enzymes were purified as described in Example 5 and used in the following assay.

For each enzyme, the conjugation reaction with each electrophilic substrate was performed by incubating 0.3 to 30 µg enzyme in 0.1 M MOPS (pH 7.0) containing 0.4 mM of the electrophilic substrate. The reaction was inititated by the addition of glutathione to a final concentration of 4 mM. After 5 to 30 min, the reaction was terminated by the addition of 45 µL acetonitrile, microfuged for 10 min to remove precipitated protein, and then the supernatent was removed and added to 65 µL of water. This sample was chromatographed on a Zorbax C8 reverse phase HPLC column (3 µm particle size, 6.2 mm×8 cm) using a combination of linear gradients (flow=1.5 mL/min) of 1% $H_3PO_4$ in water (solvent A) and 1% $H_3PO_4$ in acetonitrile. The gradient started with 5% solvent B, progressing from 5% to 75% solvent B between 1 and 10 min, and from 75% to 95% solvent B between 10 and 12 min. Control reactions without enzyme were performed to correct for uncatalyzed reaction. Quantitation of metabolites were based on an assumption that the extinction coefficient of the conjugate was identical to that of the electrophilic substrate.

Table 4 shows the activity of each enzyme measured in nmol·min$^{-1}$·mg$^{-1}$ with the seven different substrates. Activities are related to the activity of a known and previously isolated and purified GST enzyme, GH2/4 (also called GST 26) (Czarnecka et al., *Plant Molecular Biology* 3:45–58 (1984); Ulmasoz et al., *Plant Physiol* 108:919–927 (1995)).

TABLE 4

Activities of Soybean GST Enzymes

| GST Name | GST Class | Chlorimuron Ethyl | Alachlor | Atrazine | CDNB | Ethacrynic Acid | T-Stilbene Oxide | 1,2-epoxy-3-(p-nitrophenoxy)propane |
|---|---|---|---|---|---|---|---|---|
| se6.pk0037.h4 | III | 0.1 | 1 | 0.19 | 2364 | 13 | 0.06 | 1 |
| GH2/4 | III | 0.5 | 104 | 0.13 | 6030 | 8 | 7.93 | 33 |
| ses8w.pk0028.c6 | III | 0.2 | 10 | 1.40 | 515 | 17 | 4.04 | 12 |
| sr1.pk0034.c5 | III | 0.3 | 111 | 0.46 | 2545 | 14 | 0.12 | 10 |
| se6.pk0044.b7 | III | 0.1 | 0 | 0.00 | 45 | 9 | 0.00 | 1 |
| ssm.pk0067.g5 | III | 0.1 | 4 | 0.03 | 1394 | 13 | 0.49 | 19 |
| ss1.pk0020.b10 | III | 0.1 | 7 | 0.03 | 470 | 14 | 0.02 | 47 |
| GST-A | III | 0.5 | 71 | 0.03 | 1924 | 109 | 0.06 | 22 |
| ss1.pk0005.e6 | III | 1.4 | 166 | 0.00 | 2030 | 11 | 0.06 | 4 |

TABLE 4-continued

Activities of Soybean GST Enzymes

| GST Name | GST Class | Chlorimuron Ethyl | Alachlor | Atrazine | CDNB | Ethacrynic Acid | T-Stilbene Oxide | 1,2-epoxy-3-(p-nitrophenoxy)propane |
|---|---|---|---|---|---|---|---|---|
| se6.pk0048.d7 | III | 0.5 | 8 | 0.76 | 1379 | 4 | 0.07 | 9 |
| ss1.pk0002.f7 | III | 0.9 | 30 | 0.00 | 2576 | 68 | 0.16 | 10 |
| se3.03b09 | III | 4.4 | 168 | — | 14364 | 1 | 0.07 | 20 |
| se1.27b04 | I | 0.1 | 0 | 0.00 | 15 | 11 | 0.00 | 0 |
| ssm.pk0026.g11 | II | 0.0 | 0 | 0.00 | 15 | 5 | 0.04 | 2 |
| se1.pk0017.f5 | IV | 0.0 | 0 | 0.00 | 30 | 3 | 0.15 | 0 |

What is claimed is:

1. An isolated polypeptide whose amino acid sequence is selected from the group consisting of SEQ ID NO: 2, SEQ ID NO: 4, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, and SEQ ID NO: 28.

2. The isolated polypeptide of claim 1 which is encoded by a nucleic acid sequence selected from the group consisting of SEQ ID NO: 1, SEQ ID NO: 3, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27.

* * * * *